(12) United States Patent
Kelly et al.

(10) Patent No.: US 11,896,771 B2
(45) Date of Patent: Feb. 13, 2024

(54) DUAL MEMBRANE BACTERIAL VIRAL FILTER AND METHOD OF OPERATION THEREOF

(71) Applicant: KONINKLIJKE PHILIPS N.V., Eindhoven (NL)

(72) Inventors: Eamonn Martin Kelly, Carlsbad, CA (US); Matthew Perun, Carlsbad, CA (US); Christian Johnson, Carlsbad, CA (US)

(73) Assignee: Koninklijke Philips N.V., Eindhoven (NL)

( * ) Notice: Subject to any disclaimer, the term of this patent is extended or adjusted under 35 U.S.C. 154(b) by 344 days.

(21) Appl. No.: 17/320,305

(22) Filed: May 14, 2021

(65) Prior Publication Data

US 2021/0361904 A1 Nov. 25, 2021

Related U.S. Application Data

(60) Provisional application No. 63/128,259, filed on Dec. 21, 2020, provisional application No. 63/028,134, filed on May 21, 2020.

(51) Int. Cl.
 *A61M 16/10* (2006.01)

(52) U.S. Cl.
 CPC ...... *A61M 16/1055* (2013.01); *A61M 16/107* (2014.02); *A61M 16/1065* (2014.02); *A61M 2205/7509* (2013.01); *A61M 2205/7518* (2013.01)

(58) Field of Classification Search
 CPC ........ A61M 16/0057; A61M 16/0066; A61M 16/0816; A61M 16/0833; A61M 16/1045; A61M 16/105; A61M 16/1055; A61M 16/106; A61M 16/1065; A61M 16/107; A61M 2205/125; A61M 2205/7509; A61M 2205/7518; A62B 7/10; A62B 23/00; A62B 23/02; A62B 23/025
 See application file for complete search history.

(56) References Cited

U.S. PATENT DOCUMENTS

| 4,148,732 | A | 4/1979 | Burrow | |
|---|---|---|---|---|
| 5,076,933 | A | * 12/1991 | Glenn | B01D 71/10 435/308.1 |
| 5,460,172 | A | * 10/1995 | Eckerbom | A61M 16/085 128/205.12 |
| 6,035,851 | A | 3/2000 | Wallen | |
| 8,480,797 | B2 | 7/2013 | Cozean | |

(Continued)

FOREIGN PATENT DOCUMENTS

| CN | 204133993 U | 2/2015 | |
|---|---|---|---|
| WO | WO-9903525 A1 * | 1/1999 | ........ A61M 16/1045 |

(Continued)

*Primary Examiner* — Joseph D. Boecker
(74) *Attorney, Agent, or Firm* — Daniel H. Brean

(57) ABSTRACT

A gas filter device for a medical device that provides a gas to a patient including first and second gas filter elements; a body defining a cavity receives the first and second gas filter elements in series and spaced apart from, each other; first and second end walls at opposites ends of the cavity; a first coupler extending from the first end wall; a second coupler extending from the second end wall, wherein the first coupler and the second coupler define a flow channel in communication with the cavity.

20 Claims, 9 Drawing Sheets

(56) References Cited

U.S. PATENT DOCUMENTS

| | | | |
|---|---|---|---|
| 2007/0163588 A1* | 7/2007 | Hebrank | A61M 16/0069 |
| | | | 128/205.29 |
| 2015/0032020 A1 | 1/2015 | Kirsch | |
| 2018/0104431 A1 | 4/2018 | Flower | |
| 2020/0061319 A1* | 2/2020 | Hansmann | A61M 16/085 |
| 2020/0139067 A1 | 5/2020 | Chang | |
| 2021/0113793 A1 | 4/2021 | Chang | |

FOREIGN PATENT DOCUMENTS

| | | |
|---|---|---|
| WO | 2019216774 A1 | 11/2019 |
| WO | 2020082317 A1 | 4/2020 |

* cited by examiner

DUAL MEMBRANE BACTERIAL VIRAL FILTER AND METHOD OF OPERATION THEREOF

CROSS REFERENCE TO RELATED APPLICATIONS

This application claims priority to U.S. Provisional Application Ser. Nos. 63/028,134 and 63/128,259, filed on May 21, 2020 and Dec. 21, 2020, respectively, the entire contents of which are incorporated herein by reference in their entireties.

FIELD OF THE PRESENT SYSTEM

The present system relates to a bacterial and/or viral filter for a flow path of a medical device such as a ventilator or anesthesia device and, more particularly, to a dual element bacterial and/or viral filter having enhanced fault tolerance to prevent unintended contamination of the medical device, appurtenances attached thereto, and a surrounding environment and a method of operation thereof.

BACKGROUND OF THE PRESENT SYSTEM

Medical devices that provide a flow of one or more gases, such as an anesthetic device and a ventilator provide life support to humans and animals (hereinafter both of which may be commonly referred to as patients). The anesthetic device and the ventilator may employ filtration to reduce the likelihood of contamination of the patient and/or the device. For example, for respiration therapy, single use or reusable filters may be employed with the latter being subject to a greater number of failures than the former. Regardless, either type of filter may be subject to a failure which can result in the contamination of the surroundings, machinery such as the ventilator, and people such as patients and/or staff in these surroundings. Accordingly, this contamination may have adverse consequences. For example, filters are typically used to prevent bacteria and/or viruses from one patient contaminating a ventilator and then contaminating other patients who may receive respiratory therapy by the same ventilator at a later time. A filter may also be employed to maintain the cleanliness for an exhalation portion of the ventilator gas path negating the need for post-patient cleaning of the device. Typically, ventilation filters employ a single membrane/filter element which, if damaged, can render the filter ineffective which can lead to patient cross-contamination, contamination of the ventilator and of the surroundings. Unfortunately, as conventional filter failures often go unnoticed, additional care must be given to cleaning ventilators between patients to prevent this cross-contamination which can result in additional down time for cleaning and related costs. Further, even if a filter leak is detected, contamination of a ventilator and/or the surroundings is often unavoidable and may have undesirable consequences. Accordingly, embodiments of the present system overcome these and other disadvantages of conventional ventilation filters.

SUMMARY OF THE PRESENT SYSTEM

The system(s), device(s), method(s), arrangements(s), interface(s), computer program(s), processes, etc., (hereinafter each of which will be referred to as system, unless the context indicates otherwise), described herein address problems in prior art systems. Embodiments of the present system may provide a system and method for a fault tolerant dual membrane bacterial and/or viral filter that overcomes problems existing in prior systems.

In accordance with embodiments of the present system, there is disclosed a gas filter device for a medical device (100) that provides a gas to a patient. The filter device may include first and second gas filter elements that are each configured to be at least one of a viral and a bacterial filter element; a body defining a cavity configured to receive the first and second gas filter elements in series with, and spaced apart from, each other; a first end wall situated at one end of the cavity (142, 942, 1142, 1642); a second end wall situated at another end of the cavity opposite to the first end wall such that the cavity is situated between the first end wall and the second end wall; a first coupler extending from the first end wall; and a second coupler extending from the second end wall. The first coupler and the second coupler may define a flow channel in communication with the cavity. The first and second gas filter elements are sealed to an interior surface of the body such that a gas flow between the first and second couplers passes through the first and second gas filter elements.

In accordance with embodiments of the present system, the first and second couplers may be configured to only couple to the medical device in a predefined orientation. The first coupler may be configured to couple directly to the medical device and may have a different inner diameter than the second coupler which is configured to couple to ventilation tubing of the medical device such that the ventilation tubing is only couplable to the medical device with the filter device coupled therebetween. The first and second gas filter elements may be of an axial flow type. The first and second gas filter elements may be of a radial flow type. The first and second gas filter elements may each be viral and bacterial gas filter elements. The first and second gas filter elements may be of a hybrid flow type.

The filter device may include a shaft sealed to the first and second gas filter elements. The shaft may position the first and second gas filter elements relative to each other and within the cavity. The filter device may include at least one spacer situated between the first and second gas filter elements. The spacer may be configured to separate the first gas filter element from the second gas filter element. The filter device may include at least one spacer situated between at least one of the first and second gas filter elements and an adjacent one of the first and second end walls.

In accordance with embodiments of the present system, there is provided a medical device that provides a gas to a patient. The medical device may include a gas filter device including: first and second gas filter elements that are each configured to be at least one of a viral and a bacterial filter element; a body defining a cavity configured to receive the first and second gas filter elements in series with, and spaced apart from, each other; a first end wall situated at one end of the cavity; a second end wall situated at another end of the cavity opposite to the first end wall such that the cavity is situated between the first end wall and the second end wall; a first coupler extending from the first end wall; and a second coupler extending from the second end wall; a third coupler attached to the medical device and configured to releasably couple to the first coupler; and tubing configured to releasably couple to the second coupler at a first end and to provide the gas to the patient at a second end opposite to the first end. The first coupler and the second coupler may define a flow channel in communication with the cavity. The first and second gas filter elements may be sealed to an interior surface of the body such that a gas flow between the first and second couplers passes through the first and second gas filter elements.

The first and second couplers of the medical device may be configured to only couple to the third coupler and the tubing in a predefined orientation. The first coupler may be configured to couple directly to the third coupler and may have a different inner diameter than the second coupler which is configured to couple to the tubing such that the tubing is only couplable to the medical device with the filter device coupled therebetween. The first and second gas filter elements may be of an axial flow type. The first and second gas filter elements may be of a radial flow type. The first and second gas filter elements may each be viral and bacterial gas filter elements. The first and second gas filter elements may be of a hybrid flow type.

The gas filter device of the medical device may include a shaft sealed to the first and second gas filter elements. The shaft may position the first and second gas filter elements relative to each other and within the cavity. The gas filter device of the medical device may include at least one spacer situated between the first and second gas filter elements. The spacer may be configured to separate the first gas filter element from the second gas filter element. The gas filter device of the medical device may include at least one spacer situated between at least one of the first and second gas filter elements and an adjacent one of the first and second end walls (162, 150, 1150, 1162).

BRIEF DESCRIPTION OF THE DRAWINGS

It should be expressly understood that the drawings are included for illustrative purposes and do not represent the scope of the present system. It is to be understood that the figures may not be drawn to scale. Further, the relation between objects in a figure may not be to scale and may in fact have a reverse relationship as to size. The figures are intended to bring understanding and clarity to the structure of each object shown, and thus, some features may be exaggerated in order to illustrate a specific feature of a structure. In the accompanying drawings, like reference numbers in different drawings may designate identical or similar elements, portions of similar elements and/or elements with similar functionality. The present system is explained in further detail, and by way of example, with reference to the accompanying drawings which show features of various exemplary embodiments that may be combinable and/or severable wherein.

DETAILED DESCRIPTION OF THE PRESENT SYSTEM

The following are descriptions of illustrative embodiments that when taken in conjunction with the following drawings will demonstrate the above noted features and advantages, as well as further ones. In the following description, for purposes of explanation rather than limitation, illustrative details are set forth such as architecture, interfaces, techniques, element attributes, etc. However, it will be apparent to those of ordinary skill in the art that other embodiments that depart from these details would still be understood to be within the scope of the appended claims. Moreover, for the purpose of clarity, detailed descriptions of well-known devices, circuits, tools, techniques, and methods are omitted so as not to obscure the description of the present system.

The term and/or and formatives thereof should be understood to mean that only one or more of the recited elements may need to be suitably present (e.g., only one recited element is present, two of the recited elements may be present, etc., up to all of the recited elements may be present) in a system in accordance with the claims recitation and in accordance with one or more embodiments of the present system. In the context of the present embodiments, the terms "about", substantially and "approximately" denote an interval of accuracy that a person skilled in the art will understand to still ensure the technical effect of the feature in question which in some cases may also denote "within engineering tolerances". The term may indicate a deviation from the indicated numerical value of ±20%, ±15%, ±10%, ±5%, ±1%±0.5% or ±0.1%.

Embodiments of the present system may be operative with several filter flows such as axial flow type filters (hereinafter axial flow filters), radial flow type filters (hereinafter radial flow type filters), and hybrid flow type filters (hereinafter hybrid flow filters) as will be discussed below. It should be understood that features of particular embodiments illustratively described herein, may be suitably applied to other embodiments within the scope of the appended claims.

Axial Flow Filter

A description of a fault tolerant filter assembly incorporating axial flow filter elements will be discussed hereinbelow. As discussed herein, a fault tolerant filter assembly is intended to denote that the filter assembly is operable to continue an intended use as a filter, even in a case of a failure of a filtration membrane. In accordance with the present system, the fault tolerant filter assembly may continue to operate as a viral and/or bacterial filter even in a case wherein one of the viral and/or bacterial filter membranes, layers, coatings, etc., undergoes a catastrophic failure, such as a tear, puncture, etc.

Figure 1:
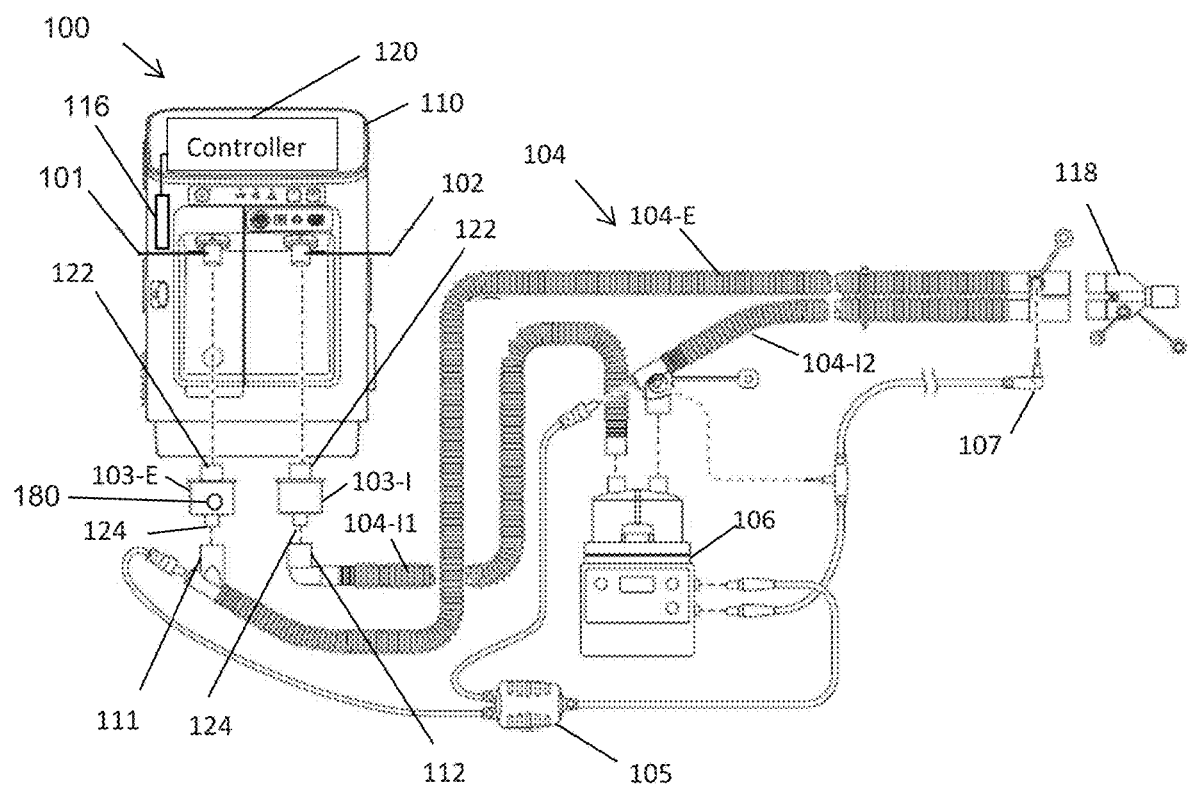
FIG. 1 shows an exploded perspective view of a portion of a ventilation system including a fault tolerant filter assembly (hereinafter FTFA) in accordance with embodiments of the present system.

FIG. 1 shows an exploded perspective view of a portion of a ventilation system 100 (e.g., ventilator, anesthesia device, etc., hereinafter system 100) including a fault tolerant filter assembly (hereinafter FTFA) in accordance with embodiments of the present system. To simplify the following discussion, a ventilator will be discussed however, it is envisioned that the same or similar system may be an anesthetic device together with or in place of the ventilator without departing from the spirit and scope of the following embodiments described. The system 100 may include a ventilator 110 having a controller 120, an expiratory inlet 101, an inspiratory outlet 102, and one or more optional sensors 116 configured to sense one or more operating parameters of the system such as pressure, flow, carbon dioxide (CO2), specific oxygen ($SpO^2$), ambient conditions (e.g., ambient temperature, pressure, and humidity, etc.), gas (e.g., inspiration flow) temperature, filter status (e.g., operating hours), filter presence, filter type (e.g., FTFA, non-FTFA, exhalation input filter, inhalation output filter, etc.), number of filter elements (e.g., 1 through N, where N is an integer), filter condition, etc., and form corresponding sensor information that may be provided to the controller 120 for further analysis as discussed herein.

For example, in some embodiments, the FTFA of any of the embodiments described herein, such as the FTFA 103-E and/or any others envisioned herein, may include an indication 180 which may identify the filter, may identify whether the filter has one, two or more filter elements, and/or other characteristics of the FTFA, such as whether the FTFA 103-E is present or absent. For example, in accordance with embodiments of the present system, the sensor 116, by sensing the indication 180, may provide such information to the controller 120 which in response, may determine that the FTFA 103-E is coupled to the ventilator 110 and thereby, the controller 120 may enable operation of the ventilator 110. Conversely, the sensor 116 may, by not sensing a presence of the indication 180, may provide such information to the controller 120 which in response, may determine that the FTFA 103-E is not coupled to the ventilator 110 and thereby, the controller 120 may disable operation of the ventilator 110. Further, in this event, the controller 120 may provide information through the user interface to connect the FTFA to the ventilator 110 to enable operation. As envisioned, other information may also be provided through the user interface by the controller 120 to correct problems associated with the sensor 116 not sensing the indication 180 and/or sensing an indication that indicates that an improper filter is coupled to the ventilator 110. Accordingly, the FTFA may include the indication 180 as one or more of a visual identifier (e.g., a bar code, a QR code, etc.), a wired and/or wireless identification/communication device (e.g., RFID tag), etc., to provide identification (ID) information to the controller 120 of the system, which information may identify the FTFA. Suitable wireless communication devices may include near field communication (NFC) devices, Bluetooth™ communication devices, WiFi communication devices, RFID tag/reader device, and/or the like.

In accordance with embodiments, the sensor 116 may receive the indication 180 indicating simply whether or not the FTFA is present such as by utilizing a light source (visible, infrared, etc.), which for example may be interrupted from reaching the sensor 116 by the FTFA, when present. Similarly, the sensor 116 may operate as a switch present on one or more of the expiratory inlet 101, the inspiratory outlet 102, and/or the patient circuit 104. For example, insertion and/or rotation of the FTFA onto the expiratory input 101 may mechanically open or close an electronic and/or mechanical switch present on the expiratory input 101. In this way, the switch may operate as the sensor 116 to provide the indication 180 that verifies whether the FTFA is present or not. In these embodiments, twisting of the FTFA after insertion of the FTFA into the corresponding receptacle, locks the FTFA in place and activates the switch. Further, in accordance with embodiments, the controller 120 may provide a visual and/or auditory prompt for an operator to confirm that the FTFA is present and/or identify the FTFA that is coupled to the ventilation system 100 (e.g., as the indication 180) prior to enabling operation of the ventilation system 100.

The controller 120, in response to the indication 180, may also obtain information related to the FTFA such as flow parameters, filter types, allowable service life (e.g., in hours and/or use, such as single use), etc., from a memory (e.g., see system 1700 and memory 1720 of FIG. 17 described below) of the system 100. For example, upon installation of a FTFA in accordance with embodiments of the present system, the controller may determine that the flow parameter for the FTFA should be between 3.10 to 3.30 cm $H_2O$ for the FTFA at a flow rate of 85 liters per minute. In these embodiments, one or more of the sensors 116 may sense the flow and subsequent resistance to flow provided by the FTFA to determine that the proper FTFA is in use. In addition, in a case wherein the proper FTFA is sensed, changes in the flow resistance over time may be subsequently monitored (e.g., periodically) to determine whether the FTFA has become damaged and/or has reached an end to its allowable service life (e.g., when the resistance to flow has increased to 6 or some other threshold value such as a maximum that the ventilation system can tolerate).

In this way, the controller 120 may for example determine current hours of use, current resistance to flow, etc., and compare this to the allowable service life. In these embodiments, for example if the current hours of use and/or resistance to flow are equal to or greater than the allowable service life/resistance to flow, the controller 120 may generate and render such information on a user interface (UI) of the system 100 (e.g., see system 1700 and rendering device 1730 of FIG. 17 described below) to inform a user of such. However, in a case wherein the controller 120 determines that the current hours of use and/or resistance to flow are are less than the allowable service life/resistance to flow, the controller may generate and render such indication (e.g., allowable filter life 4 hours, etc.) on the rendering device of the system 100.

During operation, the controller 120 may be operative to control one or more pumps of the ventilator 110 to provide an inspiratory flow and/or anesthetic gas flow to the inspiratory outlet 102 and/or may draw an expiration flow through the expiratory inlet 101. Further, in accordance with embodiments of the present system, the expiratory inlet 101 may receive an expiratory flow from the patient passively (e.g., without being drawn out by the ventilator) based on a patient's expiratory breadth.

Filters, such as an expiratory filter 103-E and an inspiratory filter 103-I (generally filters 103), may include a fault tolerant filter assembly (FTFA) in accordance with embodiments of the present system and may be coupled to an expiratory inlet port 101 and/or an inspiratory outlet port 102, respectively, so as to filter a gas flow flowing respectively therethrough. Each of the filters 103 may be the same or different from each other one. For example, one of the filters 103 may be constructed to couple to the expiratory inlet 101 while not being couplable to the inspiratory outlet 102. Similarly, another one of the filters 103 may be constructed to couple to the inspiratory outlet 102 while not being couplable to the expiratory inlet 101. Further, in accordance with other embodiments of the present system, the filters 103 may be interchangeable with each other (e.g., the filter 103 is couplable to either of the inspiratory outlet 102 and the expiratory inlet 101).

Each of the filters 103 may include first and second couplers 122, 124, respectively, for example having a cylindrical shape or the like. However, in some embodiments a frustoconical or other shape, such as a square shape, etc., is also envisioned. Each of the first and second couplers 122, 124, respectively, may be the same as or different from each other and may be configured to couple to a corresponding coupler of a patient circuit 104 as will be discussed hereinafter. For example, in accordance with embodiments of the present system, the first couplers 122 may be of a female type configuration and the second couplers 124 may be of a male type configuration and/or may have a different size/shape from each other (e.g., the first couplers 122 may have an incompatible internal and/or external diameter as compared to the second couplers 124). In accordance with embodiments of the present system, this may prevent the inadvertent coupling of hoses of a patient circuit 104 to the expiratory inlet port 101 and/or the inspiratory outlet port 102 without a filter 103 being therebetween since the hoses would not be couplable to the expiratory inlet port 101 and/or the inspiratory outlet port 102 directly. In this way, it may be ensured that the respirator is not useable without a filter 103 being in place.

In accordance with embodiments of the present system, the first and second couplers 122 and/or 124, respectively, may employ any suitable coupling to retain portions of the patient circuit 104 coupled thereto. For example, it will be assumed that an interference fit may be employed by the first and/or second couplers 122 and/or 124, respectively. However, other coupling methods such as a threaded fitting, adhesives, twist lock, a bayonet coupling, etc., may be employed as may be desired. It is further envisioned that one or more retainers may be provided to prevent one or more couplings of the breathing circuit filters from being inadvertently disconnected.

For the sake of clarity, each of the filters 103 may be assumed to be similar to each other though need not be similar to each other when two or more filters are used. Accordingly, a description of a single filter 103 may be discussed herein for the sake of clarity unless the context indicates otherwise. Differences in the filters 103 when present may be in the couplings, enclosures, and/or the filter media.

The patient circuit 104, illustratively shown as a ventilator circuit, ventilator breathing circuit, a breathing circuit, patient breathing circuit, etc., may include a patient wye 118 having inspiration and expiration branches respectively configured to be coupled to inspiration and expiration branch tubing of the patient circuit 104. For example, it is envisioned that the inspiration branch tubing may include one or more tubes such as tubes 104-I1 and 104-I2 which may be configured to couple the inspiration branch of the patient wye 108 to the inspiration outlet 102 via the filter 103-I. Similarly, the expiration branch tubing may include one or more tubes such as tube 104-E which may be configured to couple the expiration branch of the patient wye 118 to the expiratory inlet 101 via the filter 103-E. The tube 104-I1 may include a coupler 112 configured to couple to the second coupler 124 of the filter 103-I. The tube 104-E may include a coupler 111 configured to couple to the second coupler 124 of the filter 103-E using any suitable coupling such as an interference coupling. However, it is also envisioned that other types and/or methods of couplings, such as a threaded coupling, twist lock, a bayonet coupling, etc., may be employed. A safety retainer may also be provided to prevent inadvertent decoupling.

It will be assumed that the first and second couplers 122, 124, respectively, may be of different types (e.g., female and male), shapes and/or sizes from each other. For example, the first couplers 122 may be larger or smaller than the second couplers 124. This may prevent inadvertent direct coupling of portions of the patient circuit 104 to the expiratory inlet 101 and/or the inspiratory outlet 102 without one of the respective filters 103-I or 103-E placed therebetween as discussed.

The patient wye 118 may include sensors such as temperature sensors, flow sensors, gas sensors, humidity sensors, etc. which may sense corresponding conditions, form corresponding sensor information, and provide this sensor information to the controller 120 for further analysis and/or response thereto.

A flow conditioner such as a humidifier 106 may be coupled to an inspiratory circuit to receive an inspiration flow from the tube 104-I1, condition this flow (e.g., humidify the air flow), and output the conditioned flow to the patient wye 118 via the tube 104-I2. For example, the humidifier 106 may receive, from one or more sensors, one or more of humidity and temperature information sensed in the inspiration flow by the one or more sensors and may adjust humidity and/or temperature of the inspiratory flow accordingly. One or more temperature sensors, such as a temperature sensor 107, may be situated along the inspiratory and/or expiratory circuits, may sense temperature within these circuits, may form corresponding temperature sensor information, and may provide this temperature sensor information to a controller of the system, such as the controller 120, for further analysis. The controller 120 may then analyze the temperature sensor information and determine a temperature and/or humidity for the sensed gas flow. Thereafter the controller 120 may be operative to control the humidifier and/or a heater circuit (e.g., heater wire) to control humidity and/or temperature accordingly so that the gas flow may have a desired temperature and/or humidity. For the sake of clarity, it will be assumed that the controller 120 may be in communication with and/or may control operation of the humidifier 106 and/or a heater circuit in accordance with embodiments of the present system.

An optional heater wire adapter 105 may be coupled to one or more heaters to heat one or more of the inspiratory and expiratory flows that may pass through the inspiratory and expiratory tubes 104, respectively, under the control of the controller 120.

Figure 2:
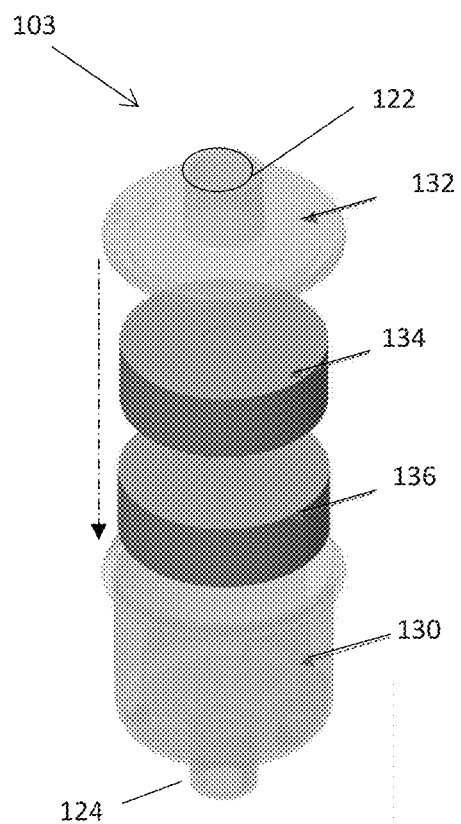
FIG. 2 shows an exploded perspective view of a portion of an FTFA in accordance with embodiments of the present system.

FIG. 2 shows an exploded perspective view of a portion of an FTFA 103 in accordance with embodiments of the present system. The FTFA 103 may include a body 130 defining a cavity configured to receive first and second filter elements 134, 136, respectively, in series, and which may generally be referred to as filter elements. The cavity may include at least one opening through which at least one of the first and second filter elements 134, 136, respectively, may pass.

Figure 3:
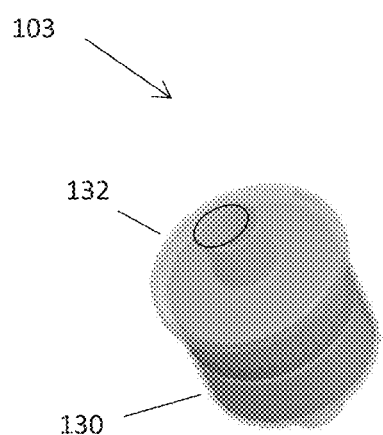
FIG. 3 shows a perspective view of a portion of an FTFA in accordance with embodiments of the present system.

A lid 132 may be configured to be coupled to the body 130 using any suitable method such as welding (e.g., friction welding, ultrasound sealing, high-frequency welding, hot gas welding, laser welding, induction welding, etc.), extruded bead sealing, solvent bonding, adhesive bonding, screw in/on (e.g., screw threads may be present on the lid 132 and/or the body 130 that screw together with corresponding portion on the opposing lid 132 or body 130 portion), etc., so as to cover the cavity of the body 130 and the filter elements contained therein and to seal (e.g., prevent inflow and outflow therebetween) the lid 132 to the body 130. It is envisioned that other methods to couple lid 132 to the body 130 such as a threaded fitting, an interference fit, a bayonet coupling, adhesives, bonds (e.g., epoxy, etc.), etc., may also or additionally be employed. The lid 132 may include a first coupler 122 and the body 130 may include a second coupler 124. The first coupler 122 and the second coupler 124 may be disposed along or substantially parallel to a common axis such as a longitudinal axis of the FTFA 103 with the first coupler 122 being configured in size and/or shape to couple only to an FTFA ventilator coupling of the present embodiments and may not couple to common ventilator (standard) line set tubing. The second coupler 124 may be configured in size and shape to be coupled to conventional ventilator line set tubing. In this way, it may be ensured that the tubing cannot be coupled to the ventilator without the FTFA 103 being in line together with the tubing for operation of the ventilator. In accordance with embodiments of the present system, other methods of ensuring that the FTFA 103 is in line together with the ventilator tubing for operation of the ventilator may be utilized such as a keying of the tubing that corresponds to the FTFA 103, a difference in shape (e.g., a first coupler being square while a second coupler is round), confirmation by a sensor (e.g., the sensor 116 shown in FIG. 1) that the FTFA 103 is present, FIG. 3 shows a perspective view of a portion of the FTFA 103 in accordance with embodiments of the present system. The lid (which may also be referred to as an upper housing) 132 is shown coupled to the body (which may also be referred to as a lower housing) 130 using any suitable method, such as the illustrative methods described herein. It is envisioned that one or more of the lid 132 and the body 130 may be formed from any suitable material such as a polymer (e.g., a plastic such as polycarbonate, acrylic, etc.), rubber, metal, glass, ceramic, etc., and may be transparent, translucent (as shown) or may be opaque as may be desired.

In accordance with the present system, the first and second filter elements 134, 136 are positioned in the body 130 in series (inline). As utilized herein, having the first and second filter elements 134, 136 in series means that airflow through the FTFA 103 must pass through each of the first and second filter elements 134, 136, successively, through one and then the other of the filter elements. Accordingly, airflow through the FTFA 103 must pass, for example, into the first coupler 122 through to the first filter element 134. After leaving the first filter element 134, the airflow must pass through the second filter element 136 before passing outward through the second coupler 124. Similarly, should the FTFA 103 be coupled such that airflow is in the opposite direction to that illustratively described above, the airflow through the FTFA 103 must pass, into the second coupler 124 through to the second filter element 136. After leaving the second filter element 136, the airflow must pass through the first filter element 134 before passing outward through the first coupler 122. In this way, since each of the first and second filter elements 134, 136 are viral filters, bacterial filters or viral and bacterial filters, the FTFA 103 can continue to operate as designed (e.g., as a viral filter, a bacterial filter or a viral and bacterial filter) even in a case wherein one of the first and second filter elements 134, 136 fails to operate (e.g., is damaged) since the other one of the first and second filter elements 134, 136 (i.e., the filter element that is not damaged) will still continue to operate as designed. Accordingly, unlike prior systems, the FTFA in accordance with the present system, is fault tolerant in that it can continue to function as designed (e.g., as a viral filter and/or a bacterial filter) even in a case wherein one of the filter elements is damaged or otherwise fails to function as designed.

Figure 4:
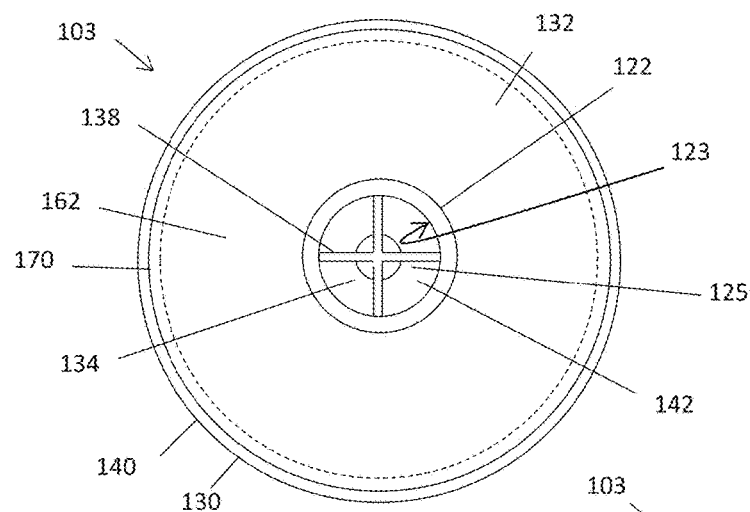
FIG. 4 shows a top view of a portion of an FTFA in accordance with embodiments of the present system.

FIG. 4 shows a top view of a portion of an FTFA 103 in accordance with embodiments of the present system. The embodiment shown may be the same, similar or somewhat different from the embodiments shown in FIGS. 1-3 and may include the same, similar or somewhat different structures including sealing methods/structures. The lid 132 (e.g., a second body portion) may have an end wall 162 and a body coupler 170 that may be configured to couple the lid 132 to the body 130 using any suitable method such as welding (e.g., friction welding, etc.). The lid 132 and the body 130 may have any suitable cross-sectional geometric configuration such as round, square, etc., and may have corresponding sizes so that they may be coupled together as discussed. With regard to the body coupler 170, although welding may be employed to couple the lid 132 to the body 130, it is envisioned that other techniques and/or methods such as bayonet fittings, threaded (e.g., screwable) fittings, interference fits, adhesives, bonds, solvent bonding, welding, etc., may be suitably employed. The body 130 may include a flange 140 which may extend about an outer periphery of the body 130 and may be configured to contact and/or couple to a portion of the lid 132 when sealed. In accordance with embodiments, the flange 140 may operate as a sealing surface for sealing the lid 132 to the body 130.

The lid 132 may include the first coupler 122 which has an inner wall 123 which defines at least part of a channel 125 leading to a cavity 142 of the body 130. Accordingly, the channel 125 may be in flow communication with the cavity 142. One or more penetration guards 138 may be situated at one or more of the channels such as the channel 125 and may be configured to prevent penetration of one or more of the first filter element 134 and/or the second filter element 136 (e.g., see FIG. 2) via the channel 125. A similar arrangement may be formed at the second coupler 124. In accordance with embodiments of the present system, the penetration guard 138 may include any suitable configuration such as a crosshair guard, a screen guard, etc., and may prevent the insertion of objects that may inadvertently pierce one of more of the filters such as the first and second filters 134, 136, respectively, (see, FIG. 2). This may prevent accidental contamination due to pierced and/or physically shifted filter elements (e.g., the first and second filter elements 134, 136 shown in FIG. 2).

Figure 5:
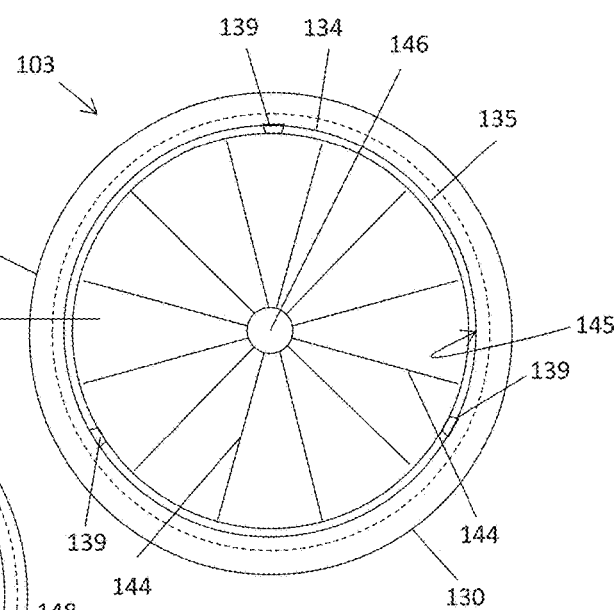
FIG. 5 shows a top view of a portion of the FTFA of FIG. 3 with a lid removed in accordance with embodiments of the present system.

FIG. 5 shows a top view of a portion of the FTFA 103 of FIG. 3 with the lid removed in accordance with embodiments of the present system. The body 103 may include an inner wall 145 which defines at least a portion of the cavity 142. The first filter element 134 may be situated within the cavity 142 and may include a peripheral seal 135 configured to seal against the inner wall 145 to prevent passage of a fluid (e.g., breadth air) therebetween. The peripheral seal 135 may be formed from any suitable material or materials such as foam, rubber, adhesive, glue, epoxy, etc. In some embodiments, the filter elements contained within the cavity 142 may be fixed in place or may be removable. The first filter element 134 may have a uniform surface (e.g., coarse or fine surface structure) as shown for example in FIG. 2 or may include one or more pleats 144 that may be arranged in any suitable fashion such as in parallel or radial orientation (as shown). An inner seal 146 may seal an inner portion of the pleats. One or more positioners such as tabs 139 may be provided and configured to maintain a position of the first filter element 134. In accordance with embodiments of the present system, the one or more positioners may be formed integrally with the body 103. The tabs 139 may be located on both sides of the first and second filter elements and may maintain a position of a respective filter element relative to each other and/or to a corresponding body portion such as the body 130. In yet other embodiments, a positioner for the respective filter elements may be formed using one or more of a detent, a grove, a notch, a step, etc.

Figure 6:
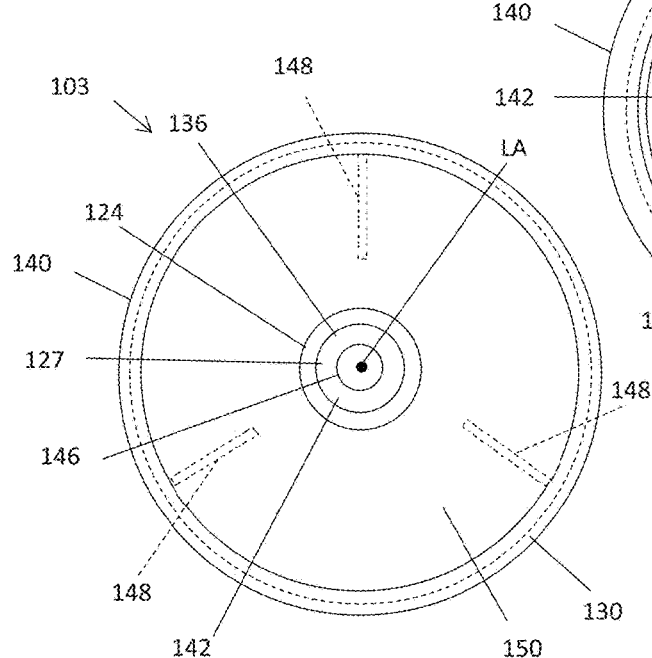
FIG. 6 shows a bottom view of a portion of an FTFA in accordance with embodiments of the present system.

FIG. 6 shows a bottom view of a portion of an FTFA 103 in accordance with embodiments of the present system. The second coupler 124 may include a channel 127 in flow communication with the cavity 142. The second filter element 136 may be situated within the cavity 142 and may be similar to (as shown), or different from, the first filter element 134 and may include a center seal 146 which may seal ends of radially arranged pleats, when present as described regarding the first filter element 134. A spacer, such as ribs 148, may be configured to space the second filter element 124 away from an end wall 150 of the body 130 and may be arranged in any desired orientation, such as radially, tangentially, etc. to a longitudinal axis (LA) of the FTFA 103. For example, a tangential orientation may be employed to prevent the ribs 148 from entering between the pleats (e.g., folds) of the corresponding filter element such as the filter element 124. It is also envisioned that the ribs 148 may also be configured to adjust (e.g., straighten) a flow of fluid through the FTFA 103.

Figure 7:
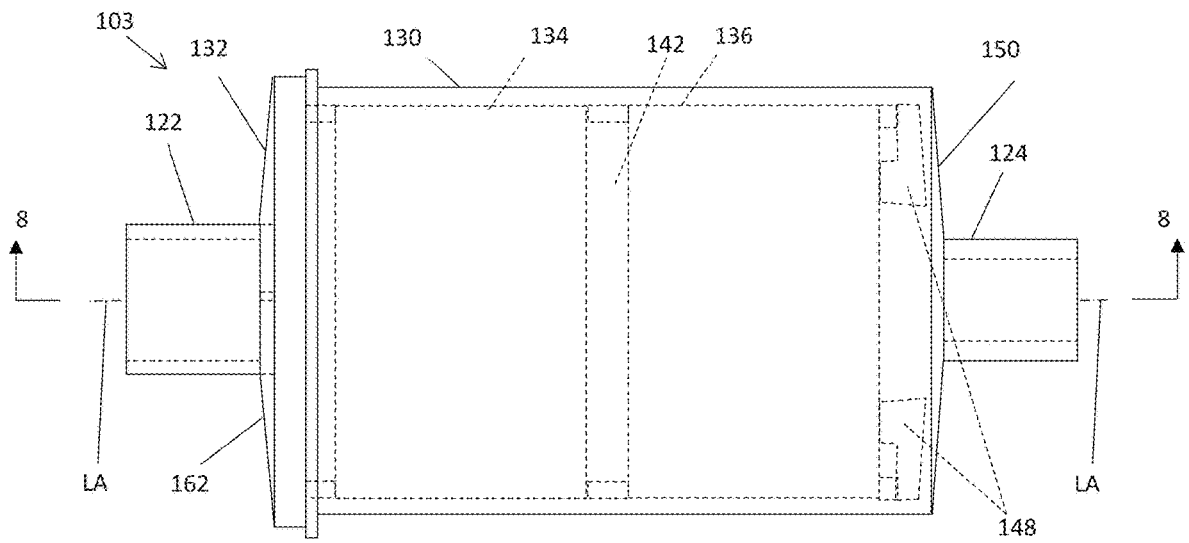
FIG. 7 shows a side view of a portion of an FTFA in accordance with embodiments of the present system.

FIG. 7 shows a side view of a portion of an FTFA 103 in accordance with embodiments of the present system that has an ellipsoid shaped outer periphery (e.g., circular, see, FIGS. 2,3). A lid 132 may include an end wall 162 and may be coupled to a body 130 such that first and second couplers 122, 124, respectively, are located opposite to each other along a longitudinal axis (LA) of the FTFA 103. Thus, in accordance with embodiments of the present system, male and female couplers, couplers of difference sizing, different shapes, different keying, etc., may be located opposite to each other. The first and second filters 134, 136, respectively, may be situated within a cavity 142 formed by the body 130. Ribs 148 may be situated apart from each other and may act to position the filter element(s) and/or guide airflow through the cavity 142 of the body 130. The other side view may be similar. Although the first and second couplers 122, 124, respectively, are shown in line with the longitudinal axis (LA), in yet other embodiments, the first and second couplers 122, 124, respectively, may be offset from the longitudinal axis (LA) and/or may be offset from each other with regard to the longitudinal axis (LA).

Figure 8:
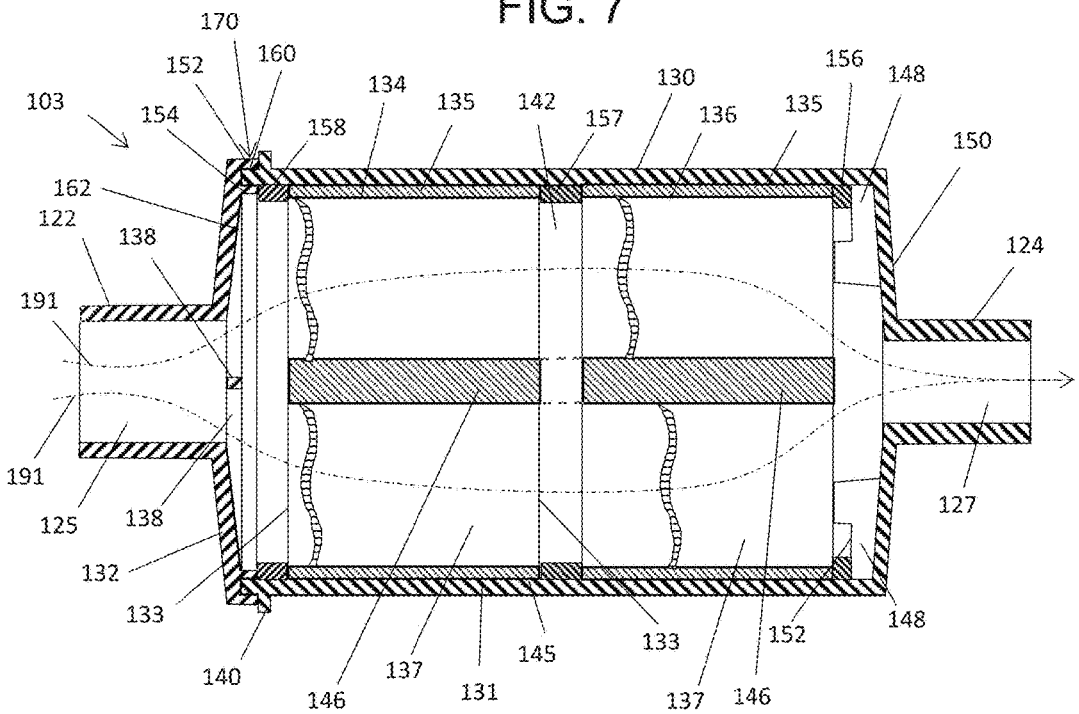
FIG. 8 shows a cutaway view of a portion of the FTFA taken along lines 8-8 of FIG. 7 in accordance with embodiments of the present system.

FIG. 8 shows a cutaway view of a portion of the FTFA 103 taken along lines 8-8 of FIG. 7 in accordance with embodiments of the present system. A body coupler 170 may include a channel 160 formed between one or more flanges 152, 154 of the lid 132 and said channel may be configured to receive and couple a side wall 131 or flange of the body 130 using any suitable method such as an interference fit, a weld, adhesives, etc. The side wall 131 may be coupled to one or more of the flanges 152 and 152 using any suitable coupling such as friction welding although other coupling method(s) such as an interference fit, a bond, a threaded fitting, tabs and notches, welding, etc., are also envisioned.

In accordance with embodiments of the present system, a sealing enhancer such as an adhesive (e.g., silicone, etc.) and/or a gasket may be employed to enhance a seal between the lid 132 and the body 130. For example, in embodiments where the FTFA 103 may be autoclavable and/or reusable, the coupling may be releasable using threads and/or an interference fit so that one or more of the filter elements may be removed and/or replaced when desired. In some embodiments, the lid 132 may be hingedly coupled to the body 130. In this way, the lid 132 and/or body 130 may be sterilized and be reused with new first and second filter elements 134,136 placed therein.

The coupler 122 may form a portion of the channel 125 which may be flow coupled to the cavity 142. The penetration guard 138 may be formed integrally with, or separately from, the lid 132 and may be configured to prevent an object (e.g., a hose, etc.) from slipping past the channel 125 into the cavity 142 where it may pierce one or more of the first and second filter elements 134, 136, respectively. The number of openings and/or mesh size of the penetration guard 138 may be varied to prevent objects of desired sizes from penetrating the first and second filter elements 134, 136, respectively.

The first coupler 122 may form a portion of a channel 125 which may be flow coupled to the cavity 142. The second coupler 124 may form a portion of a channel 127 which may be flow coupled to the cavity 142. An optional penetration guard may be provided at the channel 127 and may be configured similarly to the penetration guard 138 discussed above.

Arrows 191 may illustrate a gas flow through the FTFA 103 in one direction. However, it should be understood that the gas flow direction through the FTFA 103 may be reversed in which case the direction of gas flow may be opposite to that illustrated by the arrows 191. Gas flow may be reversed, for example, depending upon whether the FTFA 103 is coupled to the expiratory inlet or the inspiratory outlet (e.g., see, FIG. 1).

Ribs 148 may be situated radially apart from each other and may act to position respective filter element(s) and/or guide airflow through the cavity of the body 130 as described. It is also envisioned that the ribs 148 may be configured to space at least one of the filter elements, such as the second filter element 136, apart from an end wall of the body 130 and/or the lid 132 (e.g., end wall 162 and/or 150). Ribs 148 may include a notch or cutout configured to receive a spacer 156 (e.g., a ring) and/or the second filter element 136. In accordance with embodiments of the present system, the lid 132 may include ribs 148 positioned in a similar manner.

With regard to the first and second filter elements 134, 136, respectively, these filter elements may be similar to each other or be different from each other in configuration and/or materials, however, both are operational as bacterial and/or viral filters as described herein. Accordingly, a description of the first filter element 134 will be provided for the sake of clarity. However, it should be understood that the description of the first filter element 134 may apply to the second filter element 136 unless the context indicates otherwise.

In accordance with embodiments of the present system, the first filter element 134 may be an axial flow filter element with a flow substantially along a longitudinal axis (e.g., LA shown in FIG. 7) of the FTFA 103 and may include a solid and/or pleated filter media. With regard to the pleated filter media, it may include folds 133 at opposite ends of the filter element 134 so as to form pleats arranged in a radial manner as shown in the present embodiments. However, in yet other embodiments, the folds and pleats may be arranged in a parallel manner as discussed herein.

The first filter element 134 may include a peripheral seal 135 that may extend about an external periphery of the first filter element 134 and may be configured to prevent a flow of a fluid (e.g., a gas) between the first filter element 134 and an inner wall 145 of the body 130. In some embodiments, the first filter element 134 may be fixedly attached to the inner wall 145 of the body 130 using any suitable method such as an interference fit, friction boding, adhesives (e.g., hot melt, spin sealing, epoxy, etc.), etc. It is envisioned that the peripheral seal 135 may be coupled to the inner wall 145 of the body 130 using any suitable adhesive or bond.

The first filter element 134 may include any suitable filter media 137, such as a high-efficiency particulate air (HEPA) filter media, etc., which may be formed from one or more layers, for example that may be laminated upon each other, and/or other adhering method, when more than one layer is present. The filter media 137 may include a high-efficiency particulate air (HEPA) filter, etc. Suitable filter media may include polyester (e.g., folded polyester mesh, blown microfiber (BMF), spun, flat, etc.), polypropylene, and/or fiberglass, though other materials that may be formed that have desired flow, antibacterial/antiviral and/or hydrophobic properties or any combination of such properties may also be suitably employed.

The filter media 137 may be pleated to provide a larger surface area which may reduce gas flow resistance through the filter and corresponding FTFA 103. Accordingly, a gas flow resistance through the first and second filter elements 134, 136, respectively, and the FTFA 103 may be substantially equal to the gas flow resistance through a single conventional filter while the filtration capabilities of each of the first and second filter elements 134, 136 is at least equivalent to the filtration capabilities of the conventional filter.

As discussed above, the filter media 137 of the first filter element 134 may be folded at the folds 133 to form the pleats. The peripheral seal 135 and/or the inner seal 146 may seal the ends of the pleats such that a flow of liquid and/or gas passes through the filter media 137 and is filtered. In accordance with embodiments, the inner seal 146 for each of the first and second filter elements 134, 136 respectively, may be common to both and thereby, form a common shaft, shown as dashed lines for the inner seal 146, that couples and maintains spacing between and/or otherwise relative positions thereof the first and second filter elements 134, 136. In accordance with embodiments of the present system, the common shaft/seal 146 may be utilized together with any of the embodiments described herein or otherwise envisioned.

One or more spacers, such as the spacer 156 and spacers 157, 158 (generally spacers) may be configured such that the first filter element 134 may be sandwiched between, and positioned (e.g., relative to the body 130) by, the spacers 157 and 158. The second filter element 136 may be sandwiched between, and positioned by, the spacers 156 and 157. The spacers 156, 157, and/or 158, may be annular in form (e.g., ring like) and may be configured to function as a supplemental seal between the corresponding first and second filter elements and the inner wall 145 of the body 130. In some embodiments, the spacers may be secured using any suitable system such as an adhesive, a notch, a tab (e.g., optional tabs 139), an indent, a detent, etc. The spacers may be shaped similarly to the interior wall 145 of the body 130 and/or may be formed as a portion of the inner wall 145 of the body 130. In accordance with embodiments, one or more of the spacers 156, 157, 158 may be provided as a plurality of ledges formed on the inner periphery of the body 130. In another embodiments, one or more of the spacers 156, 157, 158 may be formed as a stepped housing formed on the inner periphery of the body 130. In these embodiments, the formed structure may facilitate high production fabrication in that the structure may be mass produced in a single or simplified step process from other processes that require separate placement and/or fastening of the spacers 156, 157, 158.

The spacer 157 may be sized such that the first and second filter elements 134, 136, respectively, are positioned apart from each other by a desired distance. In some embodiments, the flange 154 of the lid 132 and the ribs 148 may be spaced apart from each other such that they may impart a force upon and sandwich the spacers 156, 157, and 158 as well as the first and second filter elements 134, 136, respectively, which force may push the peripheral seals 135 of the first and second filters 134, 136, respectively, to expand and seal against the inner wall 145 of the body 130. This may provide or enhance a seal between the respective first and second filter elements 134, 136, respectively, and the inner wall 145 of the body 130.

Radial Flow Filter Elements

Figure 9:
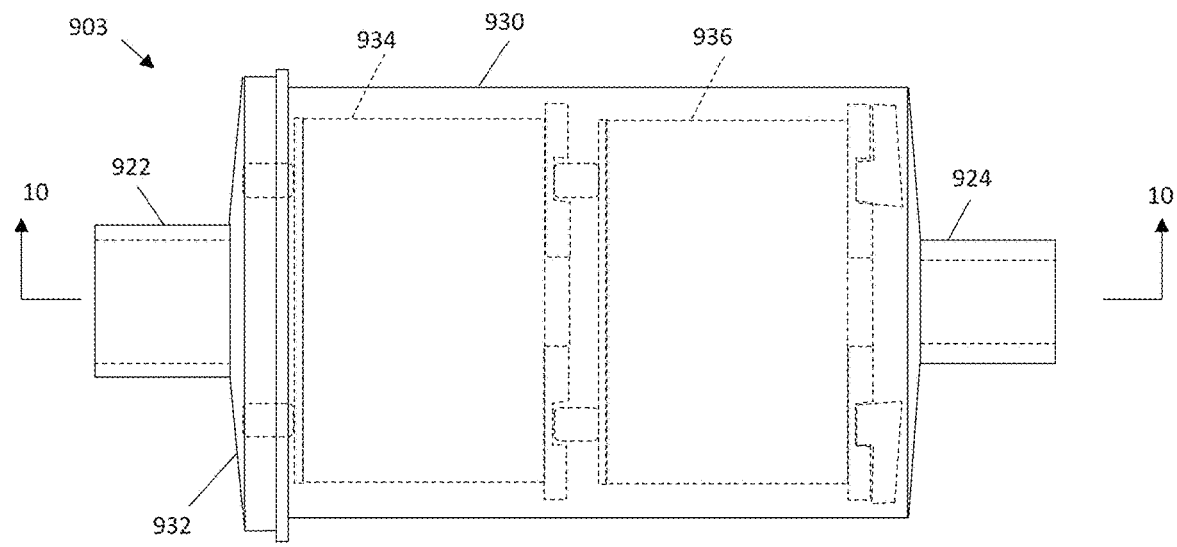
FIG. 9 shows a side view of a portion of an FTFA in accordance with embodiments of the present system.
Figure 10:
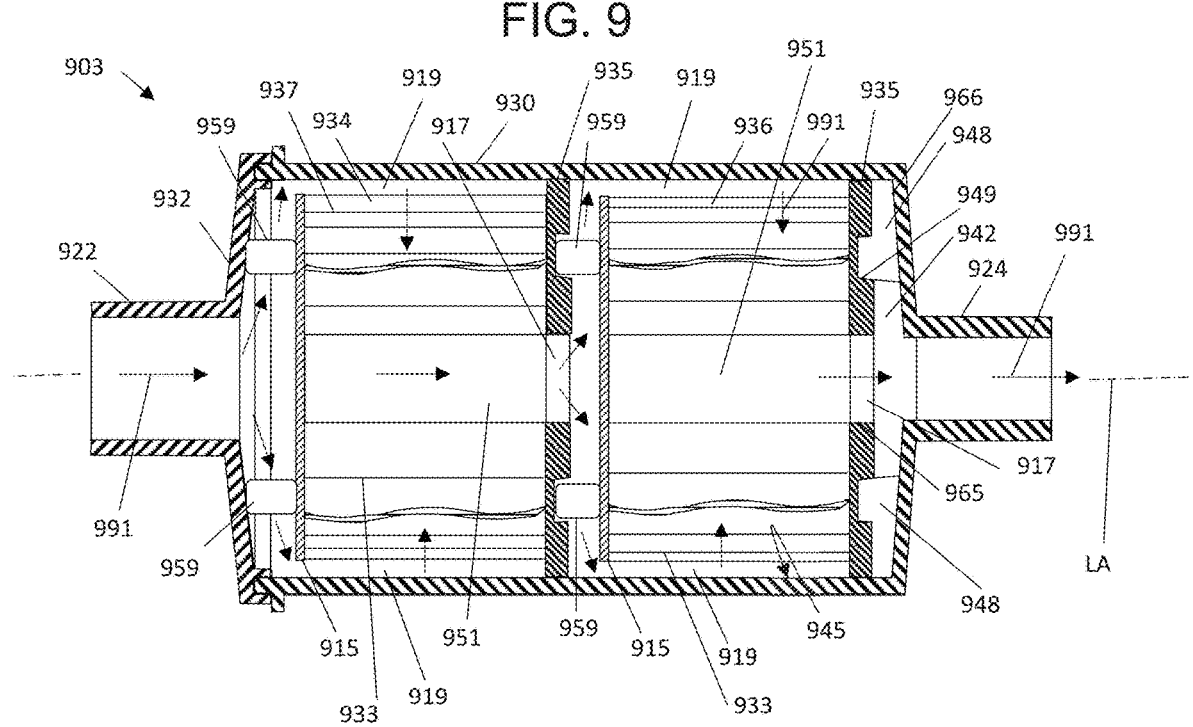
FIG. 10 shows a cutaway view of a portion of the FTFA taken along lines 10-10 of FIG. 9 in accordance with embodiments of the present system.

In accordance with embodiments of the present system, it is also envisioned that one or more (e.g., two) radial flow filter elements may also be employed as will now be discussed with reference to FIGS. 9 and 10. FIG. 9 shows a side view of a portion of an FTFA 903 in accordance with embodiments of the present system. FIG. 10 shows a cutaway view of a portion of the FTFA 903 taken along lines 10-10 of FIG. 9 in accordance with embodiments of the present system.

With reference to FIGS. 9 and 10, the FTFA 903 may include a lid 932 coupled to a body 930 such that first and second couplers 922, 924, respectively, may be located opposite to each other along a longitudinal axis (LA) of the FTFA 903. The lid 932 and the body 930 may be similar to the lid 132 and the body 130 of the embodiments shown in FIGS. 7 and 8, for example, and may form a cavity 942 configured to receive first and second filter elements 934, 936, respectively, which are both illustratively shown as radial type filter elements.

With regard to the first and second filter elements 934, 936, respectively, these filter elements may be similar to each other in configuration or may be different and may be bacterial and/or viral filters as described herein. Accordingly, a description of the first filter element 934 will be provided for the sake of clarity. However, it should be understood that the description of the first filter element 934 may apply to the second filter element 936 unless the context indicates otherwise. In the present embodiments, it will be assumed that the first filter element 934 is a radial-flow filter element with a flow substantially radial to the longitudinal axis (e.g., LA) of the FTFA 903 and may include solid and/or pleated filter media 937 situated between first and second end caps 915, 935, respectively, which may be coupled to the filter media 937 using any suitable coupling such as an adhesive, bonding, welding, etc., as described herein with regard to other filter media.

With regard to the filter media 937, as with other filter media described herein or otherwise that may be suitably applied, it may be formed from any suitable membrane or membranes and may be folded at folds 933 to form pleats arranged radially about the longitudinal axis LA so as to form an interior channel 951. The first and second end caps 915, 935, respectively, may be situated apart from each other and may be configured to seal opposed ends of the (adjacent) filter media 937. The second end cap 935 may include a wall 965 defining an opening 917 in flow communication with the interior channel 951. In some embodiments, it is envisioned that the radial flow filters may be cylindrical (as shown), conical, frustoconical and/or rectangular shaped (e.g., square shaped).

It is envisioned that the filter media 937 may be formed from one or more layers which may be laminated or otherwise adhered upon each other. These layers may be configured with different properties. For example, a first layer and/or coating may be hydrophobic, a second layer may be a viral layer (e.g., antiviral), a third layer may be a bacterial layer (e.g., antibacterial), a fourth layer may be an electrostatic layer. In some embodiments, each layer may include several filtration properties such as antiviral, antibacterial, and/or hydrophobic properties. As discussed previously, in some embodiments, the filter media 937 may include a high-efficiency particulate air (HEPA) filter, etc. Suitable filter media may include polyester (e.g., folded polyester mesh, blown micro-fiber (BMF), spun, flat, etc.), polypropylene, fiberglass, though other materials that may be formed that have desired flow and antibacterial/antiviral/hydrophobic properties may also be suitably employed. In accordance with embodiments of the present system, by folding the filter media 937 with consideration to a height and density of the folds, the total area of the filter media 937 per filter element may be greater than a cross sectional area of the cavity that is normal to the longitudinal axis LA. In accordance with one or more of the embodiments conveyed herein, the combinations of pleat angle, pleat surface area, number of pleats, etc., is optimized to achieve a certain filter performance from a given filter volume (e.g., the filter media 937 is arranged to provide a 95% filter efficiency per individual filter to fit within the FTFA while minimizing flow resistance for the FTFA encompassing two or more individual filters). In this way, the resistance to airflow may be adjusted to accommodate the first and second filter elements 934, 936 within the FTFA 903 without a need to change typical operating parameters of the respirator.

In some embodiments, portions of the first and second end caps 915, 935 may include a filter media similar to the filter media 937 so as to increase a gas flow rate of the first and second filter elements 934, 936. For example, the first end cap 915 may include a pleated filter media with pleats arranged in a radial manner similar to the pleated filter media shown in FIG. 8 or may include a filter media that is unpleated. Filters of this type may be referred to as hybrid axial-radial flow filters and may provide axial flow and/or radial flow of gas which may further lower gas flow resistance of the corresponding filter. Accordingly, in hybrid filters a flow of gas may travel through the first end cap into the interior channel (e.g., 951) in addition to the flow of gas traveling through the filter media situated between the first and second end caps. In some embodiments, it is envisioned that the hybrid filters may be cylindrical (as shown), conical frustoconical and/or rectangular.

A periphery of the first end cap 915 may be shaped, sized and/or otherwise arranged to form at least a portion of a gas flow channel 919 situated between itself and an interior wall 945 of the body 930. Similarly, the filter media 937 may be shaped, sized and/or otherwise arranged to form at least a portion of a gas flow channel 919 situated between itself and the interior wall 945 of the body 930.

The second end cap 935 may be configured to form a seal between itself and the inner wall 945 of the body 930 to prevent the flow of gas therebetween. Accordingly, the second end cap 935 may have an outer periphery that may be shaped and sized similarly to, but may be slightly larger than, the interior wall 945 of the body 930 to provide a seal (e.g., friction seal) therebetween. In yet other embodiments, the second cap 935 may have an outer periphery that may be shaped and sized similarly to the interior wall 945 of the body 930. In some embodiments, the second end cap 935 may be coupled to the inner wall 945 of the body 930 using any suitable method such as an interference fit, adhesives (hot melt, spin sealing, etc.), bonds, welds (e.g., friction welding, etc.). This coupling may support the second end cap 935 and other portions of the filter attached thereto, and may be configured to form a seal between the second end cap 935 and the inner wall 945 of the body 930 to prevent the flow of gas therebetween.

In some embodiments, the inner wall 945 of the body 930 may include one or more tabs, notches, indents, detents, steps, etc., which may be configured to maintain a position of the second end cap 935 and the filter attached thereto. The second end cap 935 may include notches or a channel 949 configured to receive one or more of ribs 948 of the body 930 and/or spacers 959.

The spacers 959, when present, may be situated apart from each other to provide for gas flow therebetween. In some embodiments, one or more of the spacers 959 may be formed separately from, or integrally with, one or more of the first and second end caps 915, 935, respectively of the corresponding filter element. In some embodiments, the spacers 959 may be coupled to one or more of the first and second end caps 915, 935, respectively, using any suitable method such as adhesives, bonds, welds, interference fits, etc. The spacers 959 may be configured to separate the first and second filter elements 934, 936, respectively, from each other and/or the adjacent lid 932 or end wall 966 of the body 930, respectively.

Airflow though the FTFA 903 is illustrated by arrows 991. As previously discussed, the airflow may also be reversed from that shown.

In some embodiments, the FTFA 903 may employ bodies having a cross sectional inner shape (e.g., within the cavity) and/or outer shape (e.g., peripheral shape) other than round. For example, an oval, and/or a rectangular (e.g., a square) cross-sectional shape may be employed in accordance with embodiments of the present system.

Figure 11:
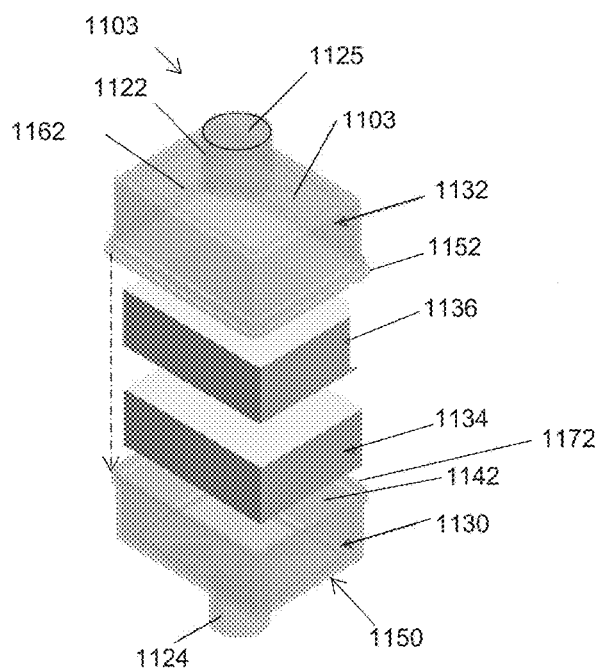
FIG. 11 shows an exploded perspective view of a portion of an FTFA in accordance with embodiments of the present system.
Figure 12:
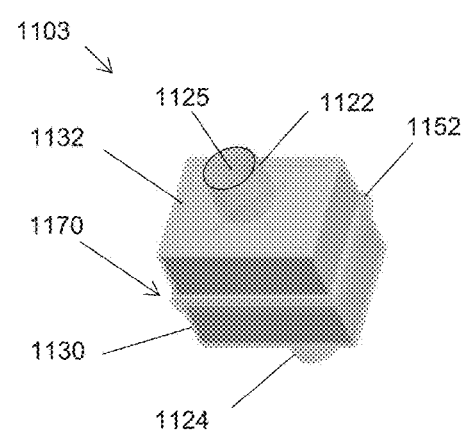
FIG. 12 shows a perspective view of a portion of the FTFA in accordance with embodiments of the present system.

An FTFA having a square cross-sectional shape will now be discussed below with reference to FIG. 11 through FIG. 16. However, as envisioned, the features described may also apply to a filter having a different cross-sectional shape. FIG. 11 shows an exploded perspective view of a portion of an FTFA 1103 in accordance with embodiments of the present system. FIG. 12 shows a front perspective view of a portion of the FTFA 1103 in accordance with embodiments of the present system. The rear perspective view may be similar to that shown.

With reference to FIGS. 11, 12, the FTFA 1103 may include first and second body portions 1130, 1132, respectively, each defining at least a portion of a cavity 1142 configured to receive first and second filter elements 1134, 1136, respectively, and which may generally be referred to as filter elements. In accordance with embodiments of the present system, the first body portion 1130 may form at least a portion of the cavity 1142 that may be configured to receive the first filter element 1136. Similarly, the second body portion 1132 may form at least another portion of the cavity 1142 that may be configured to receive the second filter element 1136. The first body portion 1130 may include a second coupler 1124 having at least one wall which defines a channel leading to the cavity 1142. Similarly, the second body portion 1132 may include a first coupler 1122 having at least one wall which defines a channel 1125 leading to the cavity 1142. The first and second body portion 1130, 1132, respectively, may be coupled to each other by a body coupler 1170 which may employ any suitable techniques or methods such as welding (e.g., friction welding, etc.) although other suitable techniques or methods are envisioned such as a threaded or screwable fitting (e.g., coupling), an interference fit, tabs and notches, glues, adhesives, bonds, etc. The body coupler 1170 may be configured to couple the first body portion 1130 to the second body portion 1132. Once coupled properly, unless damaged, there should be no detectable gas leakage through this coupling. Optional seals and/or gaskets, adhesives, welding, etc., and/or the like may be employed to enhance sealing between the first body portion 1130 and the second body portion 1132. In the present embodiments, the body coupler 1170 may include overlapping flanges such as flanges 1152 and 1172 which may form a lap joint (e.g., a double lap joint), a tongue and grove joint, etc. However, other types of joins are also envisioned such as a but joint, etc.

The first body portion 1130 may have an end wall 1150 that may form at least part of the cavity 1142 and the second body portion 1132 may have an end wall 1162 that may form at least a part of the cavity 1142. These end walls 1150 and 1162 may be positioned opposite to each other.

It is envisioned that one or more of the first body portion 1130 and the second body portion 1132 or portions thereof may be formed from any suitable material such as a polymer (e.g., a plastic such as polycarbonate, acrylic, etc.), rubber, metal, glass, ceramic, etc. and may be transparent, translucent (as shown) and/or may be opaque as may be desired.

Figure 13:
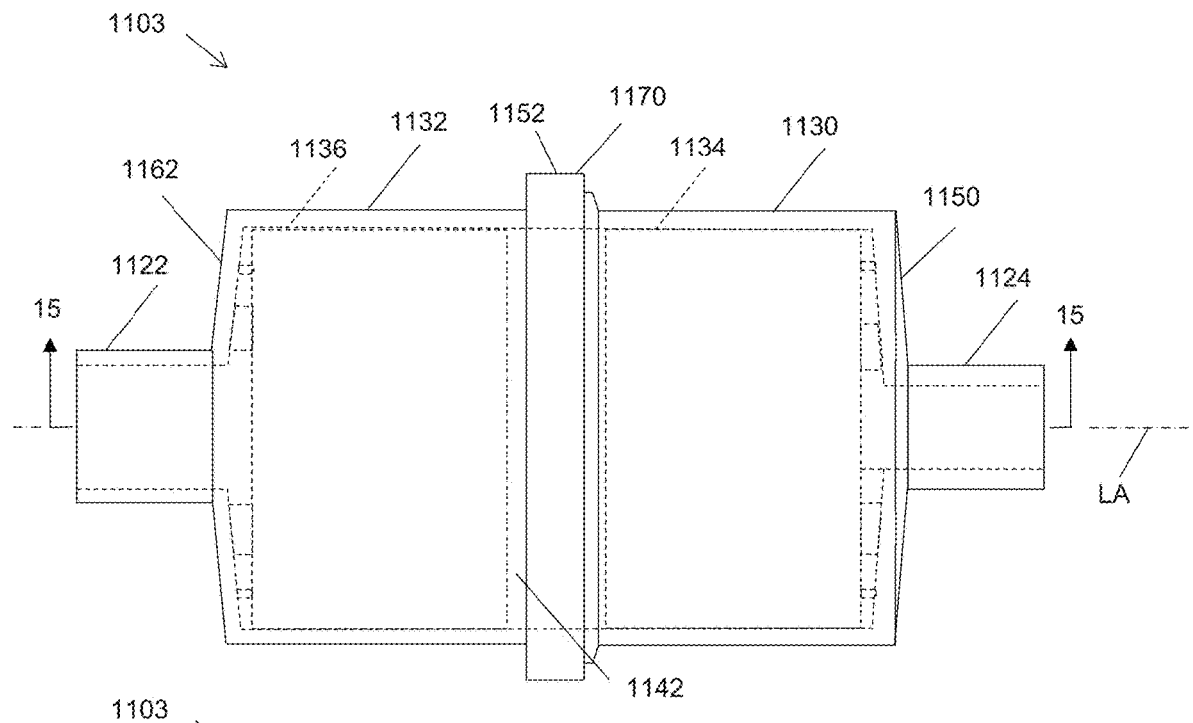
FIG. 13 shows a side view of a portion of an FTFA in accordance with embodiments of the present system.

FIG. 13 shows a side view of a portion of an FTFA 1103 in accordance with embodiments of the present system. A second body portion 1132 and a first body portion 1130 may be situated relative to each other such that the first and second couplers 1122, 1124, respectively, may be located opposite to each other along a longitudinal axis (LA) of the FTFA 1103. For example, male and female couplers (e.g., with reference to what each couples to) may be located opposite to each other. As previously discussed, the first and second couplers 1122, 1124 may also be both male or female, may be keyed differently, may be sized/shaped differently and/or other systems may be suitably applied to provide that the FTFA 1103 is coupled to the respirator or otherwise coupled to the respirator system. In this way, it may be ensured that the FTFA 1103 is coupled in a given orientation (e.g., as shown in FIG. 1) and/or that the respirator may not be operated without the FTFA 1103 coupled within the respirator circuit (e.g., between the respirator and the patient, such as between the respirator and the patient wye 118).

The first and second filters 1134, 1136, respectively, are situated within a cavity 1142 of the body 1130. Ribs may be situated apart from each other and may act to guide airflow through the cavity 1142 of the body 1130 similar or otherwise such as shown with reference to FIG. 6. The FTFA 1103 may be similar when viewed from other cross-sectional angles. A body coupler 1170 may be configured to couple the first body portion 1130 and second body portion 1132 together.

Figure 14:
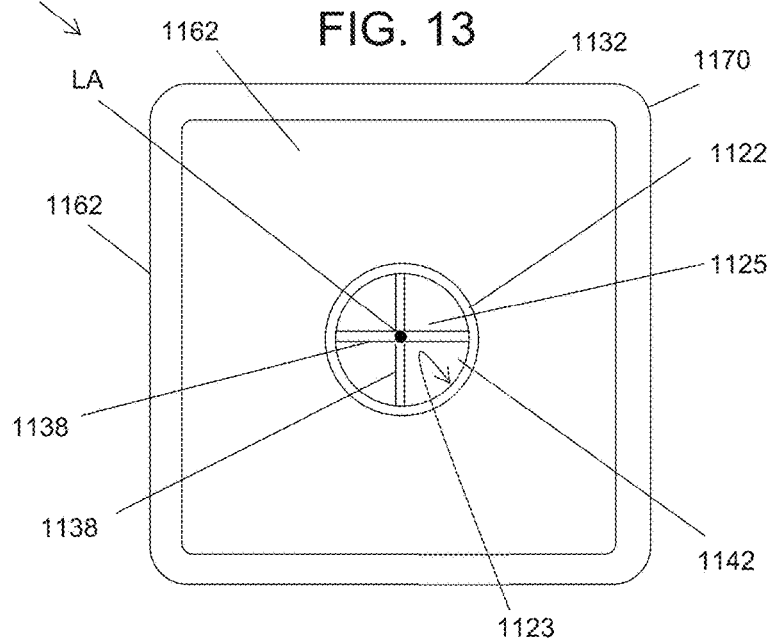
FIG. 14 shows a top view of a portion of an FTFA in accordance with embodiments of the present system.

FIG. 14 shows a top view of a portion of an FTFA 1103 in accordance with embodiments of the present system. A second body portion 1132 (which may also be referred to as an upper housing) may be coupled to a first body portion (which may also be referred to as a lower housing) as for example shown in FIG. 13 using any suitable method such as friction welding, etc. The first and second body portions, respectively, may have corresponding shapes and/or sizes such that they may be coupled together. The second body portion 1132 may include an end wall 1162 and a portion of the body coupler 1170 such as a flange. A first coupler 1122 may have an inner wall 1123 which defines at least part of a channel 1125 leading to a cavity 1142. One or more penetration guards 1138 may be situated at one or more of the channels such as the channel 1125 and may be configured to prevent penetration of the second filter element 1136 and/or the first filter element 1134. The penetration guard(s) 1138 may include any suitable configuration such as a crosshair guard, a screen guard, etc., and may prevent the insertion of objects that may inadvertently pierce one of more of the filter elements contained within the cavity 1142. A similar penetration guard may be similarly provided at the second coupler (e.g., the second coupler 1124 shown in FIG. 13).

Figure 15:
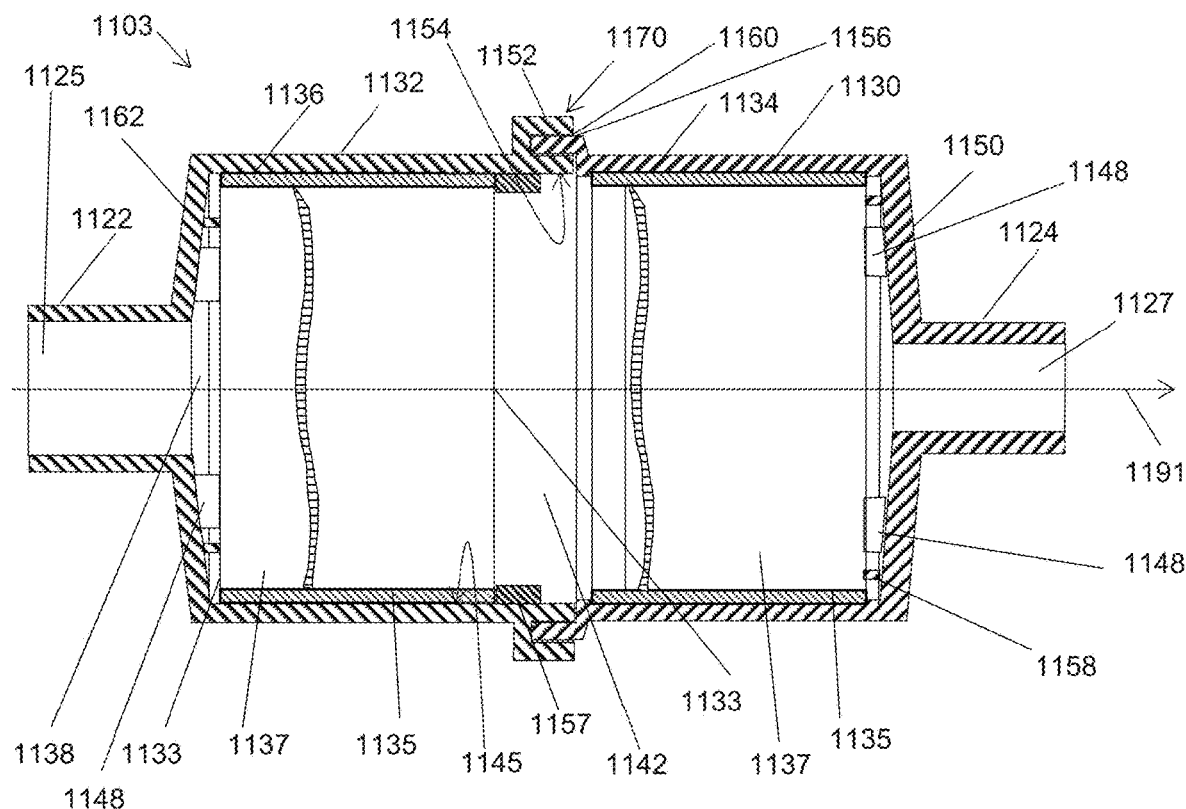
FIG. 15 shows a cutaway view of a portion of the FTFA taken along lines 15-15 of FIG. 13 in accordance with embodiments of the present system.

FIG. 15 shows a cutaway view of a portion of the FTFA 1103 taken along lines 15-15 of FIG. 13 in accordance with embodiments of the present system. The first and second body portions 1130, 1132, respectively, may be coupled to each other by the body coupler 1170. The body coupler 1170 may employ any suitable type of coupling such as a ultrasonically-welded lap joint, a tongue and grove joint and/or the like. For example, the body coupler 1170 may comprise flanges 1152 and 1154 which are separate from each other and are configured to form a channel 1160 to receive flange 1156 of the first body portion 1130. In yet other embodiments, other types of joints such as a but joint, spring fasteners, an interference fit, etc. are also envisioned. It is also envisioned that a sealing enhancer such as an adhesive (e.g., silicone, etc.) and/or a gasket may be employed to enhance a seal of the body coupler 1170. For example, in embodiments where the FTFA 1103 may be autoclavable and/or reusable, the coupling may include a releasable coupling that may provide for the opening of the cavity to insert and/or remove filter elements when desired.

The first coupler 1122 may form a portion of the channel 1125 which may be flow coupled to the cavity 1142. The penetration guard 1138 may be formed integral with, or separate from, the first or second body portions 1130, 1132, respectively. In accordance with embodiments, the penetration guard 1138 may be configured to prevent an object (e.g., a hose, etc.) from slipping past an adjacent channel, such as the channel 1125, and into cavity 1142 where it otherwise, may pierce one or more of the first and second filter elements 1134, 1136, respectively. The number of openings and/or mesh size of the penetration guard 1138 may be varied to prevent objects of desired sizes from penetrating the first and second filter elements 1134, 1136, respectively.

The coupler 1124 may form a portion of a channel 1127 which may be flow coupled to the cavity 1142. An optional penetration guard may be provided at the channel 1127 and may be configured similarly to the penetration guard 1138 discussed above.

An arrow 1191 may illustrate an exemplary gas flow direction through the FTFA which typically flows in a single direction in use. However, it should be understood that the gas flow direction through the FTFA may be reversed from that shown, for example, when coupled to a different tube (e.g., either expiratory inlet or inspiratory outlet) in which case the direction of gas flow may be opposite to that illustrated by arrow 1191.

Ribs 1148 may be situated radially apart from each other and may act to guide airflow through the cavity 1142. It is also envisioned that the ribs 1148 may be configured to position at least one of the filter elements such as the first filter element 1134 apart from the end wall 1150 of the first body portion 1130. In accordance with embodiments, another rib 1148 may also keep the second filter element 1132 away from an end wall 1162 of the second body portion 1132.

With regard to the first and second filter elements 1134, 1136, respectively, these filter elements may be similar to each other in configuration and/or materials and may be axial-type filters, radial-type filters or a hybrid axial-radial filter as described. Accordingly, a description of the first filter element 1134 will be provided for the sake of clarity. However, it should be understood that the description of the first filter element 1134 may apply to the second filter element 1136 unless the context indicates otherwise. In the present embodiments, it will be assumed that the first filter element 1134 is an axial flow filter element with a flow substantially along the longitudinal axis (e.g., LA) of the FTFA 1103 and may include solid and/or pleated filter media 1137. With regard to the pleated filter media 1137, folds 1133 defining the pleats may be arranged in a parallel manner. Embodiments of the present system may be operative with axial-flow type filters as shown, for example in FIG. 15, or radial flow filters, for example as shown with reference to FIG. 16 below.

The first filter element 1134 may include a peripheral seal 1135 that may extend about an external periphery of the first filter element 1134 and may be configured to prevent the flow of gas between the first filter element 1134 and an inner wall 1145 of the cavity 1142. In some embodiments, the first filter element 1134 may be fixedly attached to the adjacent inner wall 1145 of the cavity 1142 using any suitable method such as friction boding, adhesives (e.g., hot melt, spin sealing, epoxy, etc.), etc.

The filter media 1137 may be formed from any suitable material as discussed and may be constructed to be a bacterial and/or virus filter. The filter media 1137 may be folded over to create the folds and pleats to adjust the flow restriction. In accordance with embodiments, the filter media 1137 may be formed from one or more layers and may be attached together (e.g., laminated upon each other, etc.). For example, the filter media 1137 may be pleated to provide a larger surface area which may reduce gas flow resistance in one or more airways of the system. Accordingly, the gas flow resistance through the first and second filter elements 1134, 1136, respectively, may be substantially equal to the gas flow resistance through a conventional filter as desired. For example, a filter resistance of approximately 30-35 mm $H^2O$ @85 LPM may be achieved with dual filter-element FTFAs in accordance with embodiments of the present system which is similar to existing ventilation system single-filter designs which provide approximately 25-35 mm $H^2O$ @85 LPM with comparable efficiency (e.g., 95% efficiency or more for each of the filter elements).

In addition, the filter media 1137 may include a hydrophobic coating and/or layer to repel water (e.g., moisture in the gas flow) to resist a filtration degradation due to water saturation of the filter media 1137. For example, referring to FIG. 1, the filter 103-I may include a second filter element (e.g., the filter element closest to the tube 104-I1) with an outer layer that is closest to the tube 104-I1 that is coarser (e.g., lower filtration efficiency than other layers and/or filter elements), hydrophobic and/or that is coated with a hydrophobic coating to resist moisture infiltration of the second filter element. Similarly, the filter 103-E may include a first filter element (e.g., the filter element closest to the expiratory inlet 101) with an outer layer that is closest to the expiratory inlet 101 that is coarser (e.g., lower filtration efficiency than other layers and/or filter elements), hydrophobic and/or that is coated with a hydrophobic coating to resist moisture infiltration of the first filter element. In accordance with embodiments of the present system, a coarseness (e.g., filtration efficiency) of the filter media and/or a surface/layer thereof, may also be adjusted to provide a moisture resistance to a layer and/or surface of the filter media 1137 (e.g., the layer and/or surface of the filter media that first receives airflow may be courser than a layer and/or surface that subsequently receives the airflow).

In accordance with embodiments of the present system, wherein the filter 103-E is configured differently than the filter 103-I (e.g., having a hydrophobic layer and/or coating positioned either adjacent to or away from the expiratory inlet 101 or the inspiratory outlet 102, respectively, the corresponding filter coupling (e.g., first coupler 122) may be sized, shaped and/or otherwise configured to only receive a proper corresponding filter 103-E or 103-I. In this way, it may be ensured that the proper filter is affixed to the proper respirator coupling in embodiments wherein the filters 103-E, 103-I are configured differently. In addition, wherein the first coupler 122 is configured different from the respiratory tubing (e.g., different size, shape and/or otherwise not correspondingly compatible to each other), it may be ensured that the respirator may not be operated without a proper filter being in place between the tubing and the respirator since the tubing in these embodiments, may not be simply attached directly to the respirator.

Returning to FIG. 15, the filter media 1137 of the first filter element 1134 may be folded at folds 1133 to form the pleats. A peripheral seal 1135 may seal the ends of the pleats such that a flow of liquid and/or gas passes through the filter media 1137 and is filtered.

Spacers such as ribs 1148 and/or rings 1158 may locate one of the first and second filters 1134, 1136, respectively, relative to the adjacent end wall 1150, 1162. The ribs 1148 may further control a flow direction of gasses passing through the cavity 1142.

One or more rings such as a ring 1157 may be provided to position an adjacent filter, such as the second filter 1136, in a desired position relative to the corresponding body portion, such as the second body portion 1132 and/or relative to the first filter element 1134 (e.g., to separate the second filter 1136 from the first filter element 1134). In accordance with embodiments, a stepped inner wall 1145 (e.g., stepped inward) may also be used to position one or more corresponding filter elements.

One or more of the first and second filters 1134, 1136, respectively, may include a peripheral seal 1135 that may extend about an outer periphery of the corresponding filter element and may be configured to provide a seal between the corresponding filter element and an adjacent inner wall 1145 of the corresponding first and second body portions 1130, 1132, respectively. In accordance with embodiments, this seal may be of an interference type seal while in others it may include one or more of a weld, a bond, an adhesive, etc.

Figure 16:
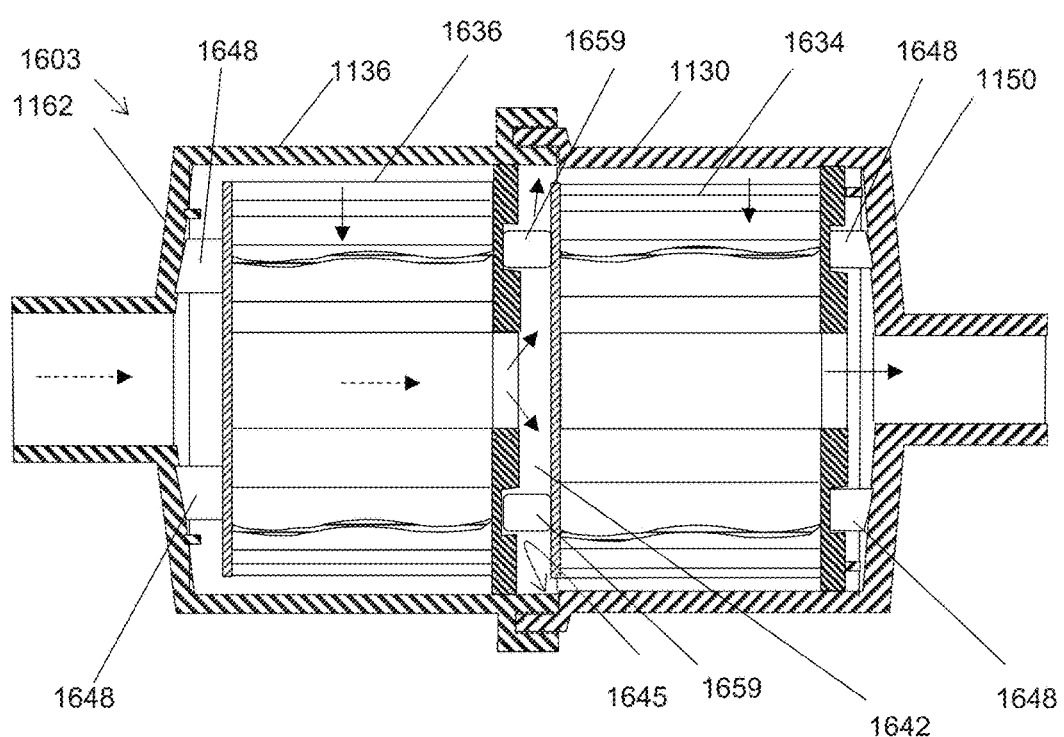
FIG. 16 shows a cutaway view of a portion of the FTFA of FIG. 15 with radial-flow filters in accordance with embodiments of the present system.

FIG. 16 shows a cutaway view of a portion of an FTFA 1603 (e.g., see, FIGS. 11, 12) with first and second radial-flow filters 1634, 1636 in accordance with embodiments of the present system. The first and second radial-flow filters 1634, 1636 may be similar to the radial-flow type first and second filters 934, 936, respectively, shown and described above with reference to FIG. 10 and may each be coupled to an inner wall 1645 of a cavity 1642 as discussed elsewhere herein. The first and second filters 1634, 1636 may be separated by spacers 1659, for example, and may be sandwiched between adjacent ribs 1648. Optional rings, steps, adhesive, etc., may be employed to position one or more of the filters 1634, 1636.

Figure 17:
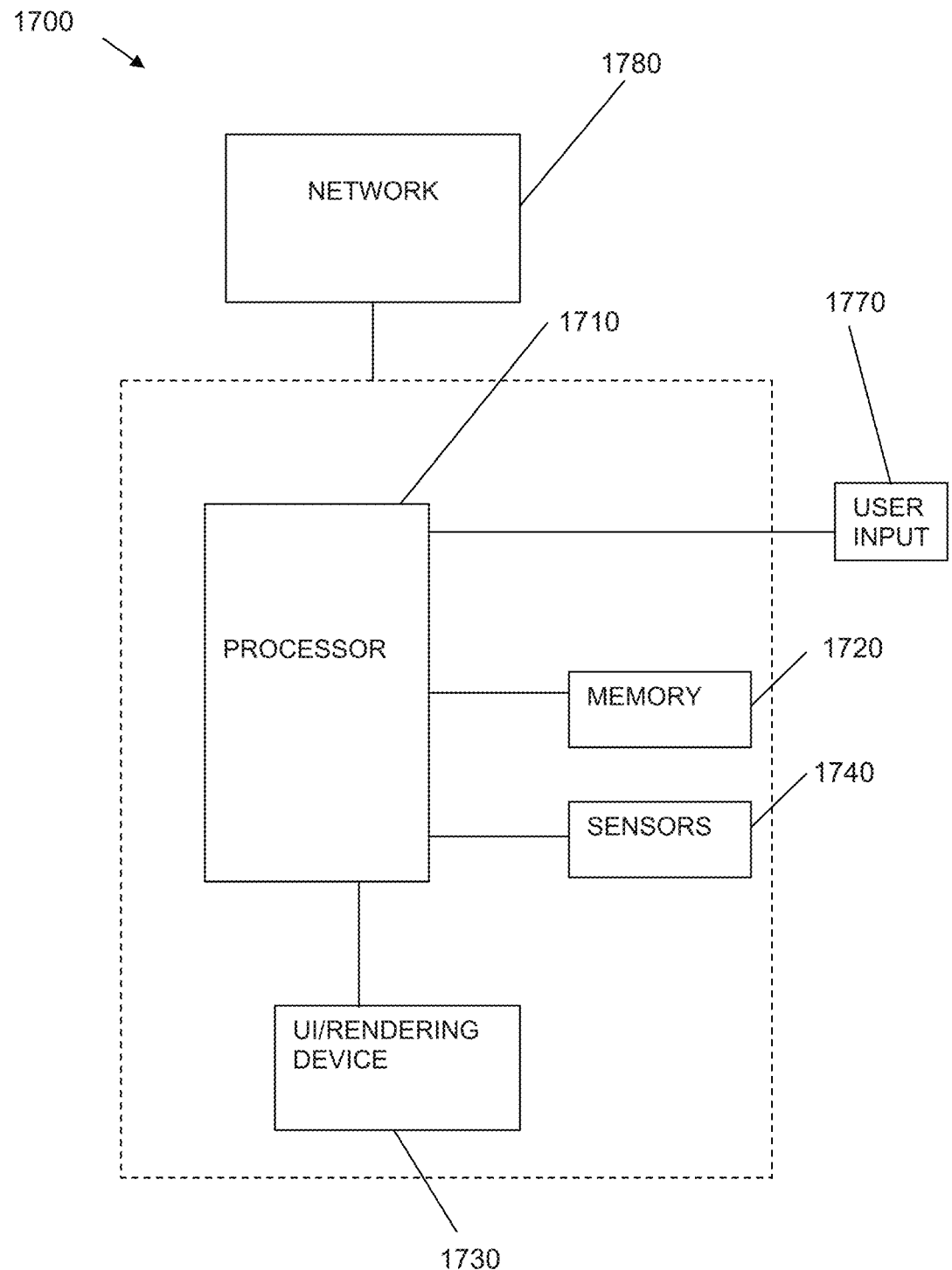
FIG. 17 shows a portion of a system in accordance with embodiments of the present system.

FIG. 17 shows a portion of a system 1700 (e.g., ventilation device, anesthesia device, etc.) in accordance with embodiments of the present system. For example, a portion of the present system may include a processor 1710 (e.g., a controller such as the controller 120 shown in FIG. 1) operationally coupled to a memory 1720, a user interface (UI) including a rendering device such as a display 1730, sensors 1740, and a user input device 1770. The memory 1720 may be any type of device for storing application data as well as other data related to the described operation. The application data and other data are received by the processor 1710 for configuring (e.g., programming) the processor 1710 to perform operation acts in accordance with the present system. The processor 1710 so configured becomes a special purpose machine particularly suited for performing in accordance with embodiments of the present system.

The processor 1710 may render the content such as still or video information on a UI of the system. This information may include information related to operating parameters, instructions, feedback, and/or other information related to an operation of the system or portions thereof. For example, the processor 1710 may receive sensor information from one or more of the sensors 1740 and compare airflow information related to current airflow through one or more portions of the system, such as one or more air filters, with threshold airflow information. In this way, the processor 1710 may determine whether the one or more air filters is operating outside of operating parameters (e.g., air filter damaged or clogged) and may render results of this determination for the convenience of a user. The sensors 1740 may include sensors of a ventilation system and/or portions thereof such as a humidifier, etc. Accordingly, the sensors 1740 may sense related parameters, form sensor information, and provide this sensor information to the processor 1710.

The user input 1770 may include a keyboard, a mouse, a trackball, or other device, such as a touch-sensitive display, which may be stand alone or part of a system, such as part of a ventilator, an anesthesia device, a laptop, a personal digital assistant (PDA), a mobile phone (e.g., a smart phone), a smart watch, a smart phone, an e-reader, a monitor, a smart or dumb terminal or other device for communicating with the processor 1710 via any operable link such as a wired and/or wireless communication link. The user input device 1770 may be operable for interacting with the processor 1710 including enabling interaction within a UI as described herein. Clearly the processor 1710, the memory 1720, display 1730, and/or user input device 1770 may all or partly be a portion of a computer system or other device such as a ventilation device, an anesthesia device, etc.

The methods of the present system are particularly suited to be carried out by a computer software program, such program containing modules corresponding to one or more of the individual steps or acts described and/or envisioned by the present system. Such program may of course be embodied in a computer-readable medium, such as an integrated chip, a peripheral device or memory, such as the memory 1720 or other memory coupled to the processor 1710.

The program and/or program portions contained in the memory 1720 may configure the processor 1710 to implement the methods, operational acts, and functions disclosed herein. The memories may be distributed, for example, between the clients and/or servers, or local, and the processor 1710, where additional processors may be provided, may also be distributed or may be singular. The memories may be implemented as electrical, magnetic or optical memory, or any combination of these or other types of storage devices. Moreover, the term "memory" should be construed broadly enough to encompass any information able to be read from or written to an address in an addressable space accessible by the processor 1710. With this definition, information accessible through a network is still within the memory, for instance, because the processor 1710 may retrieve the information from the network for operation in accordance with the present system.

The processor 1710 is operable for providing control signals and/or performing operations in response to input signals from the user input device 1770 as well as in response to other devices of a network, such as the sensor 116 discussed regarding FIG. 1, and executing instructions stored in the memory 1720. The processor 1710 may include one or more of a microprocessor, an application-specific and/or general-use integrated circuit(s), a logic device, etc. Further, the processor 1710 may be a dedicated processor for performing in accordance with the present system and/or may be a general-purpose processor wherein only one of many functions operates for performing in accordance with the present system. The processor 1710 may operate utilizing a program portion, multiple program segments, and/or may be a hardware device utilizing a dedicated or multi-purpose integrated circuit.

The processor 1710 may be operable to control one or more ventilation devices and/or other devices as described. Similarly, the processor 1710 may be operable to control peripheral devices operating for example with the ventilator such as a humidifier and/or heater circuit operating in accordance with embodiments of the present system.

Accordingly, embodiments of the present system may provide a system to monitor the state of the ventilator and/or provide a user interface for the user to control settings and/or parameters of the ventilator using a local and/or remote communication. A wireless communication link such as a Bluetooth™ or Wi-Fi™ link between portions of the ventilator and the rendering device 1730 and the system may enable rendering of system parameters on a UI of the rendering device 1730 which may also provide an entry area in which a user may change parameters such as ventilator settings, parameters, etc., of the system. Additionally, this link may be configured to link two or more ventilator systems using a two-way connection. With this connection, battery system parameters may be rendered and/or airflow rates, temperature, humidity, etc., may be displayed and/or adjusted by the user. Parameters such as temperature, voltages, specific oxygen ($SpO^2$), carbon dioxide ($CO^2$), temperature, humidity, etc., may be determined and rendered on a UI of the system for the convenience of the user. Through the UI, the user may interact to select and/or change parameters in accordance with embodiments of the present system.

Further variations of the present system would readily occur to a person of ordinary skill in the art and are encompassed by the following claims.

Finally, the above discussion is intended to be merely illustrative of the present system and should not be construed as limiting the appended claims to any particular embodiment or group of embodiments. Thus, while the present system has been described with reference to exemplary embodiments, it should also be appreciated that numerous modifications and alternative embodiments may be devised by those having ordinary skill in the art including using features that are described with regard to a given embodiment with other envisioned embodiments without departing from the broader and intended spirit and scope of the present system as set forth in the claims that follow. In addition, any section headings included herein are intended to facilitate a review but are not intended to limit the scope of the present system. In addition, the specification and drawings are to be regarded in an illustrative manner and are not intended to limit the scope of the appended claims.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function;

e) any of the disclosed elements may be comprised of hardware portions (e.g., including discrete and integrated electronic circuitry), software portions (e.g., computer programming), and any combination thereof;

f) hardware portions may be comprised of one or both of analog and digital portions;

g) any of the disclosed devices, features and/or portions thereof may be combined together or separated into further portions unless specifically stated otherwise;

h) no specific sequence of acts or steps is intended to be required unless specifically indicated; and i) the term "plurality of" an element includes two or more of the claimed element, and does not imply any particular range of number of elements; that is, a plurality of elements may be as few as two elements, and may include an immeasurable number of elements.

What is claimed is:

1. A gas filter device for a medical device that provides a gas to a patient, the filter device comprising:
first and second gas filter elements that are each configured to be at least one of a viral and a bacterial filter element, wherein the first and second gas filter elements each have a corresponding width and length;
a body defining a cavity configured to receive the first and second gas filter elements in series with, and spaced apart from, each other;
a first end wall (162, 1162) situated at one end of the cavity;
a second end wall situated at another end of the cavity opposite to the first end wall such that the cavity is situated between the first end wall and the second end wall;
first and second peripheral seals;
a first coupler extending from the first end wall; and
a second coupler extending from the second end wall,
wherein the first coupler and the second coupler define a flow channel in communication with the cavity, wherein the first gas filter element is sealed to an interior surface of the body by the first seal extending circumferentially around the width of the first gas filter element and extending tangentially to the circumferentially extension along the length of the first gas filter element, and wherein the second gas filter element is sealed to an interior surface of the body by the second seal extending circumferentially around the width of the second gas filter element and extending tangentially to the circumferentially extension along the length of the second gas filter element such that a gas flow between the first and second couplers passes through the first and second gas filter elements.

2. The filter device of claim 1, wherein the first and second couplers are configured to only couple to the medical device in a predefined orientation.

3. The filter device of claim 2, wherein the first coupler is configured to couple directly to the medical device and has a different inner diameter than the second coupler which is configured to couple to ventilation tubing of the medical device such that the ventilation tubing is only couplable to the medical device with the filter device coupled therebetween.

4. The filter device of claim 1, wherein the first and second gas filter elements are of a radial flow type, and wherein airflow prior to reaching a corresponding one of the first and second gas filter elements extends substantially radially outward to a periphery of the corresponding one of the first and second gas filter elements, then flows past the periphery, and then flows substantially radially inward away form the periphery of the corresponding one of the first and second gas filter elements.

5. The filter device of claim 1, wherein the first and second gas filter elements are each viral and bacterial gas filter elements, and wherein a corresponding one of the first and second gas filter elements closer to a source of the airflow has a surface that first contacts the airflow that is hydrophobic.

6. The filter device of claim 1, wherein the first and second gas filter elements are of a hybrid flow type.

7. The filter device of claim 1, comprising a shaft sealed to the first and second gas filter elements, wherein the shaft positions the first and second gas filter elements relative to each other and within the cavity of the body.

8. The filter device of claim 1, further comprising at least one spacer situated between the first and second gas filter elements, wherein the spacer is configured to separate the first gas filter element from the second gas filter element.

9. The filter device of claim 8, further comprising at least one spacer situated between at least one of the first and second gas filter elements and an adjacent one of the first and second end walls.

10. A medical device that provides a gas to a patient, the medical device comprising:
a gas filter device including:
first and second gas filter elements that are each configured to be at least one of a viral and a bacterial filter element wherein the first and second gas filter elements each have a corresponding width and length;

a body defining a cavity configured to receive the first and second gas filter elements in series with, and spaced apart from, each other;

a first end wall situated at one end of the cavity;

a second end wall situated at another end of the cavity opposite to the first end wall such that the cavity is situated between the first end wall and the second end wall;

first and second peripheral seals;

a first coupler extending from the first end wall; and a second coupler extending from the second end wall;

a third coupler attached to the medical device and configured to releasably couple to the first coupler; and tubing configured to releasably couple to the second coupler at a first end and to provide the gas to the patient at a second end opposite to the first end, wherein the first coupler and the second coupler define a flow channel in communication with the cavity, wherein the first gas filter element is sealed to an interior surface of the body by the first seal extending circumferentially around the width of the first gas filter element and extending tangentially to the circumferential extension along the length of the first gas filter element, and wherein the second gas filter element is sealed to an interior surface of the body by the second seal extending circumferentially around the width of the second gas filter element and extending tangentially to the circumferentially extension along the length of the second gas filter element such that a gas flow between the first and second couplers passes through the first and second gas filter elements.

11. The medical device of claim 10, wherein the first and second couplers are configured to only couple to the third coupler and the tubing in a predefined orientation.

12. The medical device of claim 11, wherein the first coupler is configured to couple directly to the third coupler and has a different inner diameter than the second coupler which is configured to couple to the tubing such that the tubing is only couplable to the medical device with the filter device coupled therebetween.

13. The medical device of claim 10, wherein the first and second gas filter elements are of a radial flow type and wherein airflow prior to reaching a corresponding one of the first and second gas filter elements extends substantially radially outward to a periphery of the corresponding one of the first and second gas filter elements, then flows past the periphery, and then flows substantially radially inward away from the periphery of the corresponding one of the first and second gas filter elements.

14. The medical device of claim 10, wherein the first and second gas filter elements are each viral and bacterial gas filter elements, and wherein a corresponding one of the first and second gas filter elements closer to a source of the airflow has a surface that first contacts the airflow that is hydrophobic.

15. The medical device of claim 10, wherein the first and second gas filter elements are of a hybrid flow type.

16. The medical device of claim 10, wherein the gas filter device comprises a shaft sealed to the first and second gas filter elements, wherein the shaft positions the first and second gas filter elements relative to each other and within the cavity of the body.

17. The medical device of claim 10, wherein the gas filter device comprises at least one spacer situated between the first and second gas filter elements, wherein the spacer is configured to separate the first gas filter element from the second gas filter element.

18. The medical device of claim 17, wherein the gas filter device comprises at least one spacer situated between at least one of the first and second gas filter elements and an adjacent one of the first and second end walls.

19. A gas filter device for a medical device that provides a gas to a patient, the filter device comprising:

first and second gas filter elements that are each configured to be at least one of a viral and a bacterial filter element;

a body defining a cavity configured to receive the first and second gas filter elements in series with, and spaced apart from, each other;

a first end wall (162, 1162) situated at one end of the cavity;

a second end wall situated at another end of the cavity opposite to the first end wall such that the cavity is situated between the first end wall and the second end wall;

a first coupler extending from the first end wall;

a second coupler extending from the second end wall;

wherein the first coupler and the second coupler define a flow channel in communication with the cavity, and wherein the first and second gas filter elements are sealed to an interior surface of the body such that a gas flow between the first and second couplers passes through the first and second gas filter elements; and a shaft sealed to the first and second gas filter elements, wherein the shaft positions the first and second gas filter elements relative to each other and within the cavity.

20. A medical device that provides a gas to a patient, the medical device comprising:

the filter device of claim 19; and an airflow exit wherein the airflow exits the medical device, wherein the airflow exit is sized to fit only one of the first and second couplers.

* * * * *